United States Patent [19]
Baskerville et al.

[11] Patent Number: 6,143,503
[45] Date of Patent: Nov. 7, 2000

[54] USE OF A RIBOZYME TO JOIN NUCLEIC ACIDS AND PEPTIDES

[75] Inventors: Donald Scott Baskerville, Newton; David P. Bartel, Brookline, both of Mass.

[73] Assignee: Whitehead Institute for Biomedical Research, Cambridge, Mass.

[21] Appl. No.: 09/291,837

[22] Filed: Apr. 14, 1999

Related U.S. Application Data

[60] Provisional application No. 60/082,256, Apr. 17, 1998.
[51] Int. Cl.$^7$ .............................. C12Q 1/68; C12P 19/34; C07H 21/04
[52] U.S. Cl. ........................... 435/6; 435/91.2; 530/300; 530/350; 536/23.1; 536/24.1
[58] Field of Search ................................. 536/23.1, 24.1; 435/6, 91.2; 530/300, 350

[56] References Cited

U.S. PATENT DOCUMENTS 5,728,818  3/1998  Wincott et al. ..................... 536/25.3

FOREIGN PATENT DOCUMENTS

WO 93 03172  2/1993  WIPO.
WO 95 11922  5/1995  WIPO.

OTHER PUBLICATIONS

Sigma Catalog, pp. 1030–1034 and 1818, 1993.
Zhang et al., Nature 390, 96–100 (1997).
Lohse et al., Nature 381, 442–444 (1996).
Wang, Z. and Rana, T.M., "RNA–protein interactions in the Tat–trans–activation response element complex determined by site–specific photo–cross–linking," *Biochemistry* 37(12) :4235–4243, (1998).
Naryshkin, N.A., et al. "Chemical cross–linking of the human immunodeficiency virus type 1 Tat protein to synthetic models of the RNA recognition sequence TAR containing site–specific trisubstituted pyrophosphate analogues," *Biochemistry* 36(12) :3496–3505, (1997).

Ye, X., et al., "Molecular recognition in the bovine immunodeficiency virus Tat peptide–TAR RNA complex," *Chem Biol* 2(12) :827–840, (1995).

Bartel, D.P. and Szostak, J.W., "Isolation of new ribozymes from a large pool of random sequences," *Science* 261(5127) :1411–1418 (1993).

Farrow, M.A., et al., "Site–specific cross–linking of amino acids in the basic region of human immunodeficiency virus type 1 Tat peptide to chemically modified TAR RNA duplexes," *Biochemistry* 37(9) :3096–3108, (1998).

Melekhovets, Y.F. and Joshi, S., "Fusion with an RNA binding domain to confer target RNA specificity to an RNase: design and engineering of Tat–RNase H that specifically recognizes and cleaves HIV–1 RNA in vitro," *Nucleic Acids Res* 24(10) :1908–1912, (1996).

Liu, Y., et al., "Visualizing a specific contact in the HIV–1 Tat protein fragment and trans–activation responsive region RNA complex by photocross–linking," *J. Biol. Chem.* 271(17) :10391–10396, (1996).

Srinivasan, J., et al., "A docking and modelling strategy for peptide–RNA complexes: applications to BIV Tat–TAR and HIV Rev–RBE," *Fold Des* 1(6) :463–472, (1996).

(List continued on next page.)

*Primary Examiner*—Kenneth R. Horlick
*Attorney, Agent, or Firm*—Hamilton, Brook, Smith & Reynolds, P.C.

[57] ABSTRACT

Engineered mRNA useful in producing libraries of engineered mRNAs, polypeptide-engineered mRNA conjugates and diverse encoded polypeptide libraries, as well as novel ribozymes that join an mRNA to the translation product of the mRNA and methods of identifying members of diverse encoded polypeptide libraries which exhibit a desired activity. Also described are polypeptide-nucleic acid tag conjugates, methods of producing the conjugates and uses therefor.

65 Claims, 9 Drawing Sheets

OTHER PUBLICATIONS

Hager, A.J. and Szostak, J.W., "Isolation of novel ribozymes that ligate AMP–activated RNA substrates," *Chem. Biol.* 4(8):607–617, (1997).

Zhang, B. and Cech, T.R., "Peptide bond formation by in vitro selected ribozymes," *Nature* 390(6655):96–100, (1997).

Roberts, R.W. and Szostak, J.W., "RNA–peptide fusion for the in vitro selection of peptides and proteins," *Proc. Natl. Acad. Sci. USA*, 94(23):12297–12302 (Nov. 1997).

Nemoto, N., et al., "In vitro virus: bonding of mRNA bearing puromycin at the 3'–terminal end to the C–terminal end of its encoded protein on the ribosome in vitro," *FEBS Lett* 414(2):405–8 (Sep. 1997).

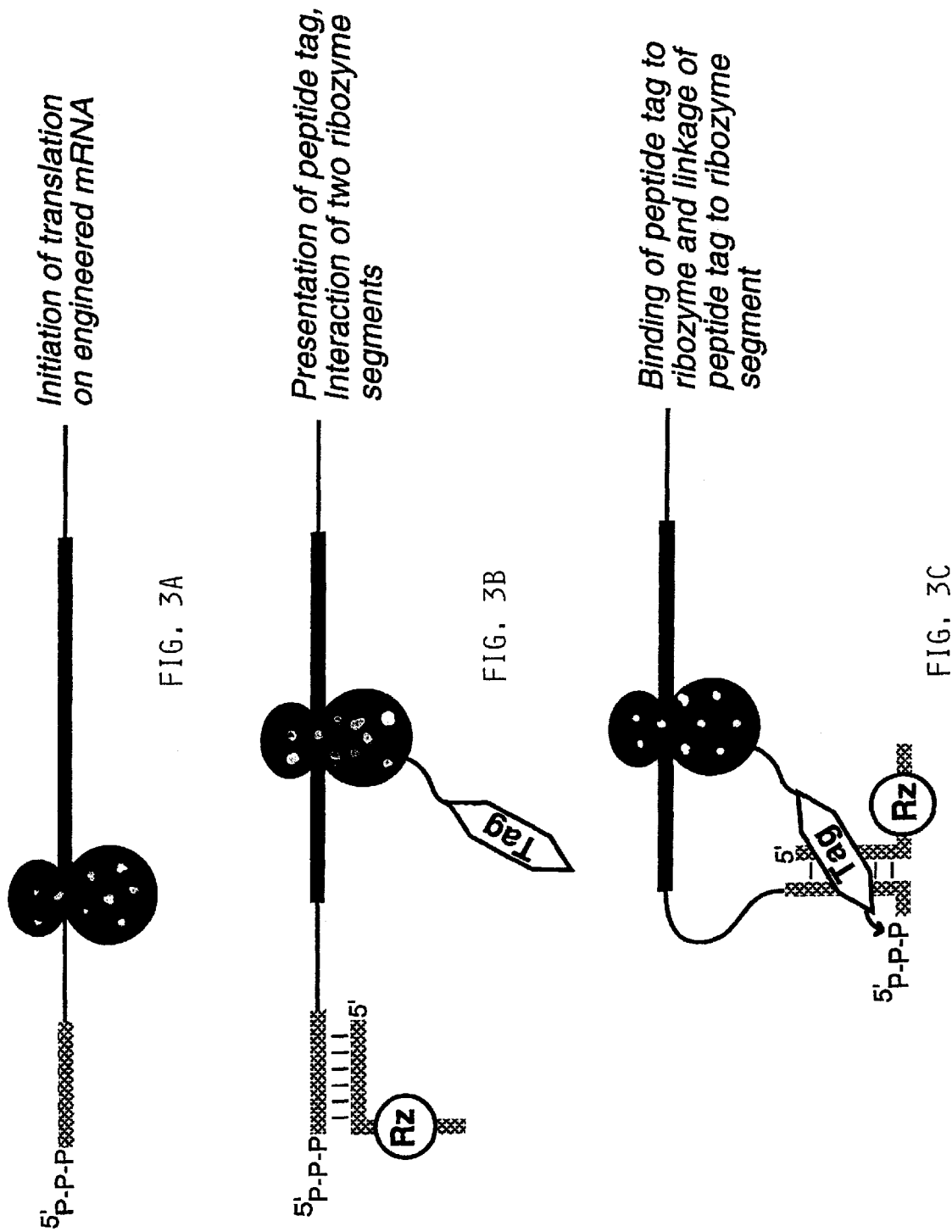

A polypeptide with a peptide tag at its amino terminus

A nucleic acid tag that is attached to the part of the ribozyme that becomes joined to the peptide tag The remainder of the ribozyme The ribozyme joins the polypeptide to a nucleic acid tag Polypeptides with specific nucleic acid tags

USE OF A RIBOZYME TO JOIN NUCLEIC ACIDS AND PEPTIDES

RELATED APPLICATION(S)

This application claims the benefit of U.S. Provisional Application 60/082,256, entitled A New Method for Generating Diverse Libraries of Encoded Polypeptides, by Donald Scott Baskerville and David P. Bartel, filed Apr. 17, 1998. The entire teachings of U.S. 60/082,256 are incorporated herein by reference.

FUNDING

The subject invention was supported in part by Postdoctoral Fellowship Grant number DBJ-9750048 from the National Science Foundation and the Alfred P. Sloan Foundation.

BACKGROUND OF THE INVENTION

Large combinatorial libraries of biopolymers are starting points for isolating new enzymes, binding motifs and other useful molecules. For example, current technologies can generate populations of nucleic acids with complexities on the order of $10^{15}$ molecules and then isolate and identify a single molecule with a desired activity. Random polypeptide populations have greater chemical diversity than do polynucleotides, making them an attractive alternative to nucleic acids. Current systems are limited in their ability to easily generate large complex libraries of polypeptides that are in a form that allows the isolation and identification of rare molecules with a desired activity.

SUMMARY OF THE INVENTION

Described herein are ribozymes which join a nucleic acid (RNA or DNA) to a polypeptide, the resulting products and uses for these products. In one embodiment of the invention, a ribozyme which joins RNA to a polypeptide is used to produce a diverse library (or collection) of encoded polypeptides, in which library members are polypeptide-engineered mRNA conjugates. The polypeptide-engineered mRNA conjugates comprise an engineered mRNA, which is described below, and the translation product of the engineered mRNA. Diverse libraries of encoded polypeptides of the present invention can be screened to identify and isolate library members which are conjugates in which the polypeptide exhibits desired characteristics or properties (e.g., binding to a molecule or compound of interest, enzymatic activity). In a second embodiment, a ribozyme which joins RNA to a polypeptide is used to produce polypeptides, each of which is linked to and, thus, tagged by, a specific nucleic acid. The resulting nucleic acid-tagged polypeptides comprise a polypeptide (which is to be tagged by a nucleic acid); a peptide substrate of the ribozyme used to join the nucleic acid to the polypeptide; ribozyme RNA and a nucleic acid tag. The presence of the nucleic acid tag is useful, for example, in detecting, isolating, separating, identifying or purifying the polypeptide to which it is linked and in changing the properties (e.g., solubility) of the polypeptides. An unlimited number of nucleic acid tags can be made, which overcomes a limitation of presently-available methods, which rely on a small repertoire of affinity tags, as well as sometimes incompatible incubation protocols for each tag. Such ribozymes, methods of using them, the resulting products and methods of identifying, detecting, isolating, separating, purifying and/or using these products are described in detail herein.

One embodiment of the present invention relates to the use of ribozymes described herein to produce a diverse library or collection of encoded polypeptides in which the members are polypeptide-engineered mRNA conjugates; engineered mRNA; methods of producing diverse libraries of encoded polypeptides; methods of identifying target members of the libraries which are polypeptide-engineered mRNA conjugates which exhibit a desired activity or characteristic; target members and the components (polypeptide fragment and engineered mRNA fragment) of target members; and isolated ribozymes which join an mRNA to the translation product of the mRNA.

Polypeptide-engineered mRNA conjugates of the present invention comprise an engineered mRNA and the translation product of the engineered mRNA. Engineered mRNA of the present invention is one component of the conjugates which make up the diverse libraries of encoded polypeptides and is used to produce the conjugates. Members of the diverse library are polypeptide-engineered mRNA conjugates produced by in vitro translation of engineered mRNA. The engineered mRNA comprises: (a) a ribozyme RNA which specifically covalently links to a peptide; (b) a coding region for the peptide, referred to as a peptide tag, with which the ribozyme RNA specifically covalently links; (c) a coding region for a diverse polypeptide; and (d) two PCR primer-binding sites. In one embodiment, the engineered mRNA comprises, in order from the 5' to the 3' end, a ribozyme segment which comprises a first PCR primer binding-site and a motif that interacts specifically with a peptide; a coding region for the peptide with which the motif interacts; a coding region for a diverse polypeptide and a second PCR primer-binding site.

The ribozyme RNA which specifically covalently links to a peptide is present in (is a component or segment of) a ribozyme which is either a contiguous sequence (the entire ribozyme is a contiguous sequence) or comprised of two noncontiguous components: one which comprises the ribozyme RNA which specifically covalently links to the peptide and one which comprises the remainder of the ribozyme sequence. In the latter case, the ribozyme RNA which covalently links to a peptide is of sufficient length and appropriate composition to covalently link to the peptide tag in the presence of the remainder of the ribozyme sequence, under the conditions used to produce the diverse libraries. The remaining ribozyme sequence is the ribozyme sequence which, in combination with the component which covalently links to the peptide tag, makes up the complete ribozyme. The ribozyme sequence or segment which covalently links to the peptide tag can be as short as one nucleotide in length and can be from any location (e.g., 5' end, internal segment, 3' end) in the ribozyme. In one embodiment, the ribozyme segment includes from one to about 18 nucleotides, such as from the first to about the 18th nucleotide (from the 5' end) of a ribozyme. In further embodiments, the ribozyme segment is the first 13 to 18 nucleotides (from the 5' end) of the ribozyme. (e.g., the first 13, 14, 15, 16, 17, or 18 nucleotides from the 5' end). The other component is the remaining ribozyme sequence (the remainder of the ribozyme which is necessary to form a functional ribozyme.). The two ribozyme components interact with one another to form a functional (complete) ribozyme under the conditions used to produce diverse libraries of encoded polypeptides. The 5' end of the ribozyme RNA optionally comprises three phosphate groups or an mRNA cap, such as a 7-methyl guanosine triphosphate. Optionally, the engineered mRNA further comprises an RNA linker between the ribozyme sequence and the tag coding region. Optionally, the engineered mRNA additionally comprises a coding region for a peptide linker; this coding region is positioned between the coding region for the peptide tag and the diverse coding region. Further, the engineered mRNA can include an optional ribosome stalling site, which is located between the coding region for the diverse polypeptide segment and the second PCR primer-binding site.

In one embodiment, the engineered mRNA comprises (in order from 5' to 3'): 1) a ribozyme sequence (also referred to as which comprises a first PCR primer-binding site and a motif that interacts specifically with a peptide; 2) a coding region for a peptide (referred to as a peptide tag), with which the ribozyme motif interacts specifically; 3) a coding region for a diverse polypeptide segment and 4) a second PCR primer-binding site. In addition, in this embodiment, the engineered mRNA can include one or more of the following optional components: 5' phosphate groups; an RNA linker between the ribozyme sequence and the tag coding region: a coding region for a peptide linker (positioned between the tag coding region and the diverse coding region) and a ribosome stalling site which is located between the coding region for the diverse polypeptide segment and the second PCR primer-binding site.

In a specific embodiment, the motif that interacts specifically with a peptide is modified Bovine Immunodeficiency Virus-1 (BIV-1) TAR RNA and the peptide tag is one with which BIV-1 TAR RNA interacts specifically by virtue of the BIV-1 Tat sequence embedded within the tag, e.g., the Tat tag peptide 1, also referred to as the Tat tag (SEQ ID NO.: 1: MSYSGPRPRGTRGKGRRIRRGGK), or the Tat 2 tag peptide, also referred to as the Tat 2 tag (SEQ ID NO.: 2: MKYSGPRPRGTRGKGRRIRRGGK). In both the Tat tag peptide and the Tat 2 tag peptide, the underlined amino acids are a BIV-1 Tat peptide (SEQ ID NO.: 3). The sequence of the modified BIV-1 TAR RNA is: 5' GGA CAG CUC GCA UUC UCG UGU AGC U (SEQ ID NO.: 4).

Also the subject of this invention are isolated ribozymes or ribozyme portions which join an mRNA to a polypeptide, such as the translation product of the mRNA. Such ribozymes comprise a motif which specifically covalently links to a peptide, with the result that the ribozyme is joined specifically to the peptide. Ribozymes of the present invention can be a contiguous sequence or can be comprised of two noncontiguous components which interact with one another to form the complete ribozyme, under the conditions used to produce diverse libraries of encoded polypeptides. The two noncontiguous components are a ribozyme segment which specifically covalently links to a peptide and a ribozyme segment which comprises the remaining ribozyme. As a result, an mRNA which comprises such a ribozyme and a coding region for the peptide with which the ribozyme interacts will be joined to the translation product of the mRNA (through binding and then covalent linkage of the ribozyme RNA and the peptide). An example of a ribozyme that contains a motif that interacts specifically with a peptide (modified TAR RNA) and joins itself specifically to certain peptides (e.g., the Tat tag peptide or the Tat 2 tag peptide) is specifically described herein.

Members of the encoded polypeptide libraries, referred to as target members, which have desired characteristics (e.g., binding, enzymatic, antigenic characteristics) are also the subject of this invention, as are methods of identifying target members. Polypeptide fragments and ribonucleoprotein fragments of members of the libraries, particularly fragments of target members of the libraries, are further subjects of this invention.

The present invention provides a method and reagents for generating diverse libraries of encoded polypeptides and for identifying and isolating members of the libraries, particularly members which exhibit rare characteristics and occur in small numbers.

A second embodiment of the present invention relates to the use of ribozymes to join a desired nucleic acid tag to a polypeptide to produce a polypeptide tagged with the desired (specific) nucleic acid. As described above, the ribozyme can comprise a motif which specifically covalently links to a peptide. The resulting polypeptide-nucleic acid tag conjugate is a subject of the present invention, as are its components, collections or libraries of such conjugates and methods of making and using the conjugates. In this embodiment, a ribozyme which joins a polypeptide to a nucleic acid is used as follows to produce polypeptide-nucleic acid tag conjugates: A polypeptide, also referred to as a polypeptide of interest (e.g., a polypeptide to be identified, detected, separated, isolated, purified, altered in characteristic(s)), which is tagged with the peptide substrate of the ribozyme used, is joined covalently, as described below, to the nucleic acid tag through the action of the ribozyme. The resulting polypeptide-nucleic acid tag conjugate comprises: the polypeptide, the peptide substrate of the ribozyme used, a ribozyme RNA and the nucleic acid tag. In one embodiment, a polypeptide-nucleic acid tag conjugate comprises a polypeptide-nucleic acid tag conjugate comprising: (a) a polypeptide of interest; (b) a peptide tag linked to the polypeptide of interest, wherein the peptide tag is the substrate of a ribozyme; (c) a ribozyme or a segment of a ribozyme for which the peptide tag of (b) is a substrate, wherein the ribozyme or ribozyme segment is covalently linked to the peptide tag; and (d) a nucleic acid tag, wherein the nucleic acid tag is linked to the ribozyme or ribozyme segment. In one embodiment, the peptide is linked to the 5' terminus of the ribozyme RNA and the nucleic acid tag extends from the 3' terminus of the ribozyme RNA. The peptide substrate of the ribozyme is referred to herein as the peptide tag. As a result of the specific interaction of the peptide tag on the polypeptide with the ribozyme for which the peptide tag is a substrate, the polypeptide component is covalently linked to the nucleic acid tag. This technique has several clear advantages over other methods of tagging proteins. For example, because the peptide tag and the RNA component of the ribozyme interact specifically with each other, the ribozyme tagging reaction can be performed in a mixture of biological molecules, such as in a crude cell lysate, as well as in vivo. In addition, because there is no limit on the number of different possible nucleic acid tags, an essentially unlimited number of different (uniquely or specifically) tagged polypeptides can be produced. Once produced, the tagged proteins can be mixed and then detected simultaneously, using, for example, hybridization to DNA arrays.

Another embodiment of the present invention is a method of producing a polypeptide-nucleic acid tag conjugate, comprising: (a) combining: (1) a polypeptide of interest which bears a peptide tag wherein the peptide tag is a substrate for ribozyme RNA; (2) ribozyme RNA, wherein the ribozyme RNA specifically covalently links to the peptide tag of (a)(1) in the presence of the remainder of the ribozyme and has linked thereto a nucleic acid tag; (3) the remainder of the ribozyme, thereby producing a combination; and (b) maintaining the combination under conditions appropriate for ribozyme RNA of (a)(2) to associate with ribozyme RNA of (a)(3), forming a functional ribozyme that specifically covalently links the peptide tag to ribozyme RNA of (a)(2), whereby the polypeptide-nucleic acid tag conjugate is produced.

Another embodiment of the present invention is a method of separating a polypeptide from a mixture of polypeptides, comprising: (a) tagging the polypeptide at its amino terminus with a peptide tag, thereby producing a polypeptide-peptide tag, wherein the peptide tag is a substrate for ribozyme RNA, thereby producing a mixture comprising the polypeptide-peptide tag; (b) combining the mixture produced in (a) with (1) ribozyme RNA which bears a nucleic acid tag and specifically covalently links to the peptide tag in the presence of the remainder of the ribozyme and (2) the remainder of the ribozyme, under conditions appropriate for ribozyme (b) (1) to specifically interact with its peptide substrate thereby forming a covalent link with the peptide and tagging the polypeptide with the nucleic acid tag, whereby a mixture comprising a polypeptide-nucleic acid tag conjugate is formed; (c): combining the mixture formed in (b) with a nucleic acid which is a binding partner for the nucleic acid tag of the polypeptide-nucleic acid tag conjugate, whereby the binding partner hybridizes with the nucleic acid tag of the conjugate, forming a polypeptide-nucleic acid tag conjugate with the binding partner bound thereto; and (d) separating the polypeptide-nucleic acid tag conjugate with the binding partner bound thereto from the product of (c), whereby the polypeptide is separated from the mixture of polypeptides. In one embodiment, the binding partner is bound to a solid surface.

The present invention also relates to a method of detecting a polypeptide of interest in a mixture, wherein the method comprises: (a) combining a mixture to be assessed for the presence of the polypeptide-nucleic acid tag conjugate with a binding partner for the nucleic acid tag, wherein the binding partner (1) is a nucleic acid sequence sufficiently complementary to the nucleic acid tag that the binding partner and the nucleic acid tag of the conjugate bind to one another and remain bound under the conditions used and (2) is bound to a solid surface and wherein the combining occurs under conditions appropriate for binding of the nucleic acid tag and the binding partner and (b) detecting whether binding of the nucleic acid tag and the binding partner occurred, wherein if binding is detected, the polypeptide of interest is detected. In one embodiment, the binding partner or the nucleic acid tag is labeled with a detectable moiety (e.g., a chemical moiety, radioactivity) and detection of binding is carried out by detecting the presence of the detectable moiety.

BRIEF DESCRIPTION OF THE DRAWINGS

FIGS. 3A–3D represent schematically one embodiment of the invention in which a ribozyme comprised of two non-contiguous components is used to produce polypeptide-engineered mRNA conjugates, and a representative conjugate produced by the method. In FIG. 3A, initiation of translation on engineered mRNA is represented; the linear cross-hatched area represents a ribozyme segment which specifically covalently links to the peptide tag. In FIG. 3B, presentation of the peptide tag and interaction of the two ribozyme segments is shown schematically; the L-shaped cross-hatched area represents the remaining segment of the ribozyme, which is bound to the ribozyme RNA which specifically covalently links to the peptide tag. In FIG. 3C, binding of the peptide tag to the ribozyme and the reaction covalently linking the peptide tag to the ribozyme segment are represented. In FIG. 3D, the resulting encoded polypeptide is represented schematically. The cross-hatched area represents ribozyme RNA.

FIG. 8A depicts a polypeptide (with a peptide tag at its amino terminus) which is to be tagged with a nucleic acid and a two-part ribozyme, in which the portion of the ribozyme that becomes joined to the polypeptide is joined to (has been extended by) a nucleic acid tag to be linked to the polypeptide. In FIG. 8B, the three components represented in FIG. 8A are combined and incubated under conditions appropriate for function of the ribozyme used and, as illustrated, the ribozyme specifically recognizes the amino terminal sequence (peptide tag) of the polypeptide and attaches the nucleic acid tag to the peptide tag. FIG. 8C shows that, because there is no limit to the number of different nucleic acid tags that can be used, many different polypeptides can be linked to nucleic acid tags and the resulting tagged polypeptides then mixed together for simultaneous use.

DETAILED DESCRIPTION OF THE INVENTION

The present invention relates to a ribozyme which joins a polypeptide to a nucleic acid, products resulting from the joining activity of the ribozyme, methods of making the products and uses therefor. As described herein, the present invention can be seen as relating to two embodiments in which the ribozymes of the present invention are used: one in which the ribozyme functions to join an mRNA to its translation product and is useful to produce diverse libraries of encoded polypeptides and one in which the ribozyme functions to join a polypeptide of interest to a nucleic acid which acts as a tag, producing polypeptide of interest-nucleic acid tag conjugates, in each of which the nucleic acid tag is different (specific), thus permitting identification, detection, separation, isolation, purification and/or alteration of characteristics of the polypeptide of interest. Ribozymes of the present invention, as well as the two embodiments, are described in detail herein and also represented in the figures.

Ribozymes

Figure 5A:
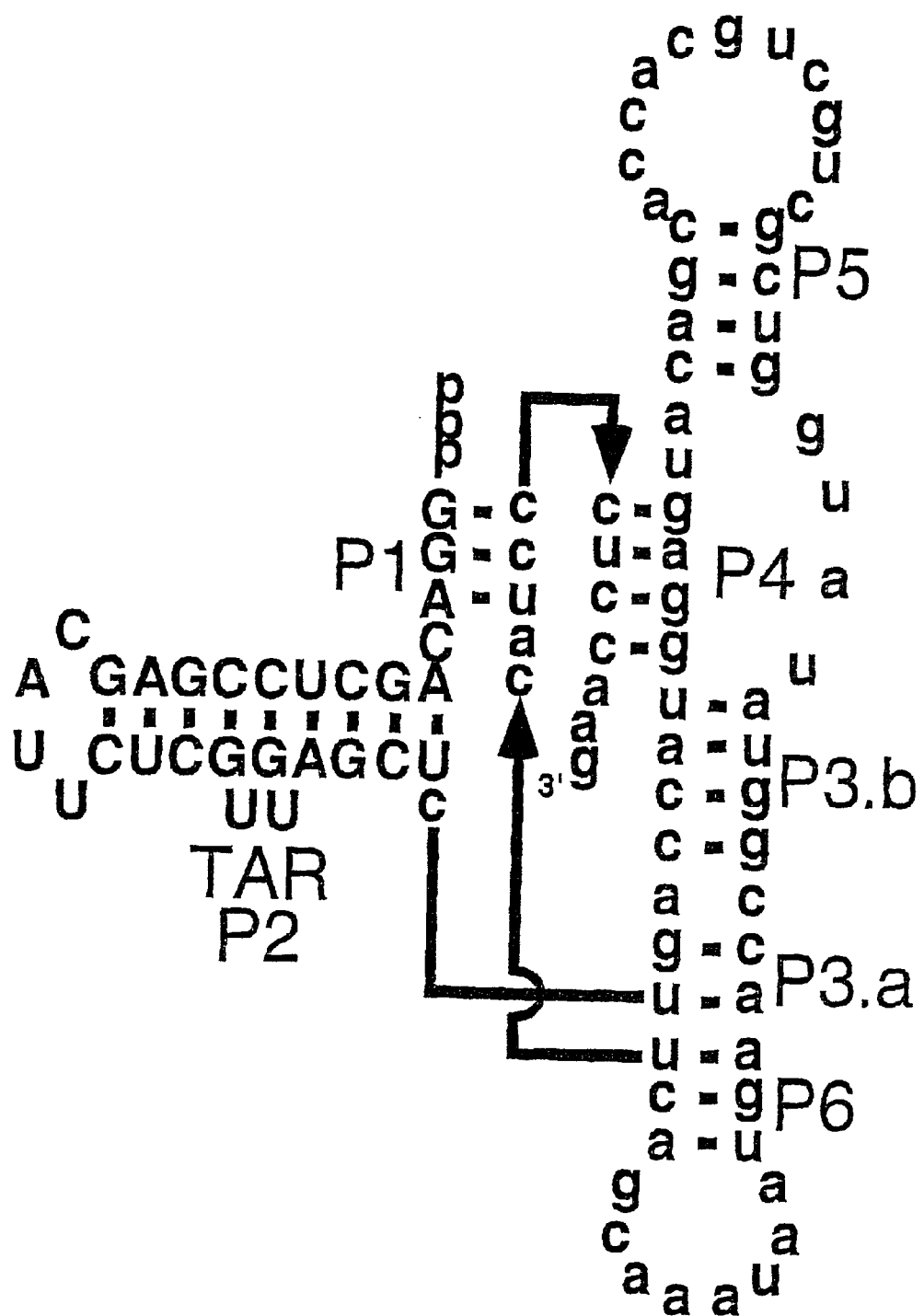
FIG. 5A is an example of a ribozyme sequence (SEQ ID NO.: 5) that attaches itself to the modified BIV Tat peptide. Upper case letters represent the residues of the modified TAR RNA motif. This ribozyme was isolated using the scheme shown in FIG. 4.
Figure 5B:
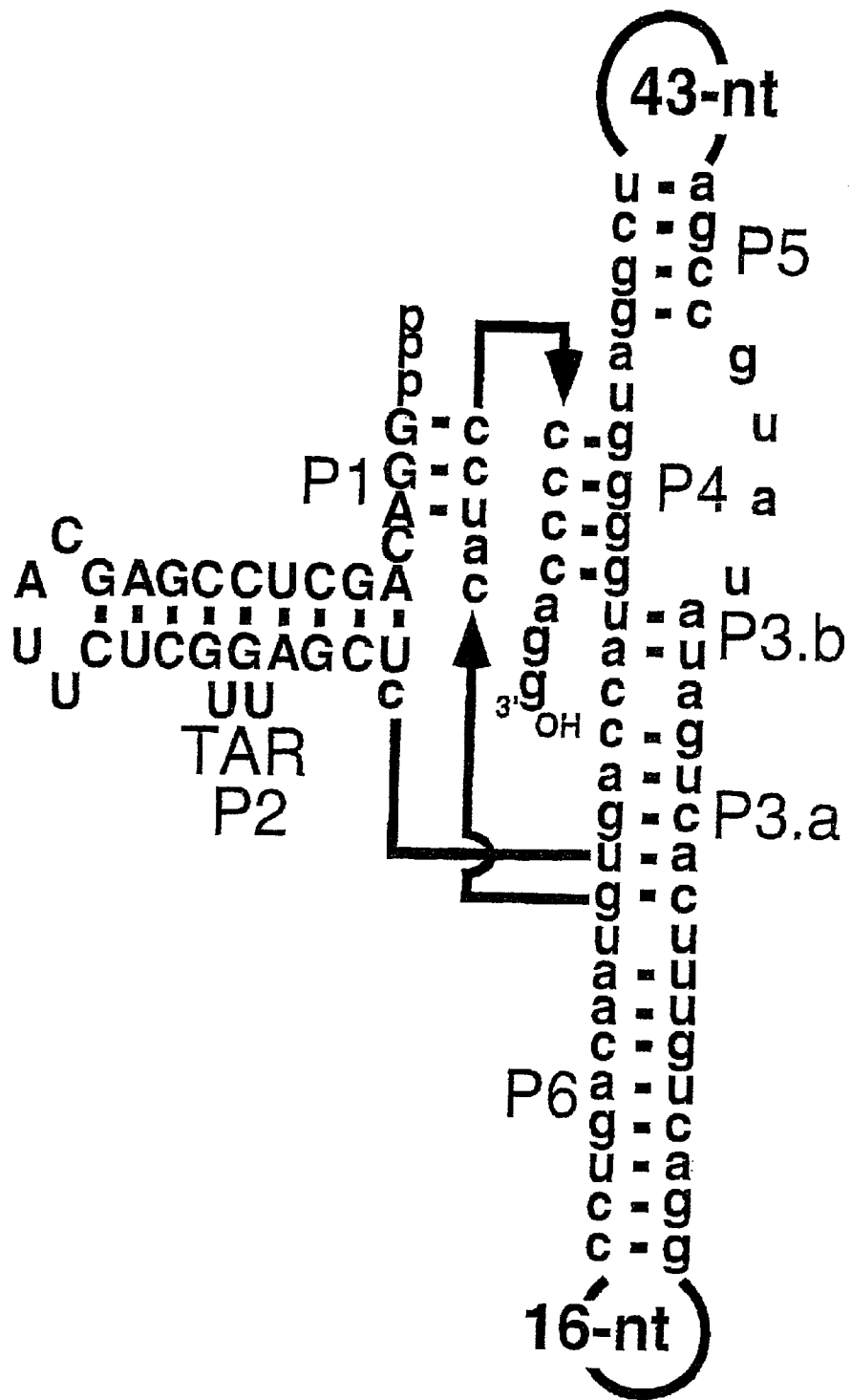
FIG. 5B is an example of a ribozyme sequence (SEQ ID NO.:6) that attaches itself to the modified BIV-1 Tat peptide. Upper case letters represent the residues of the modified TAR RNA motif.
Figure 6:
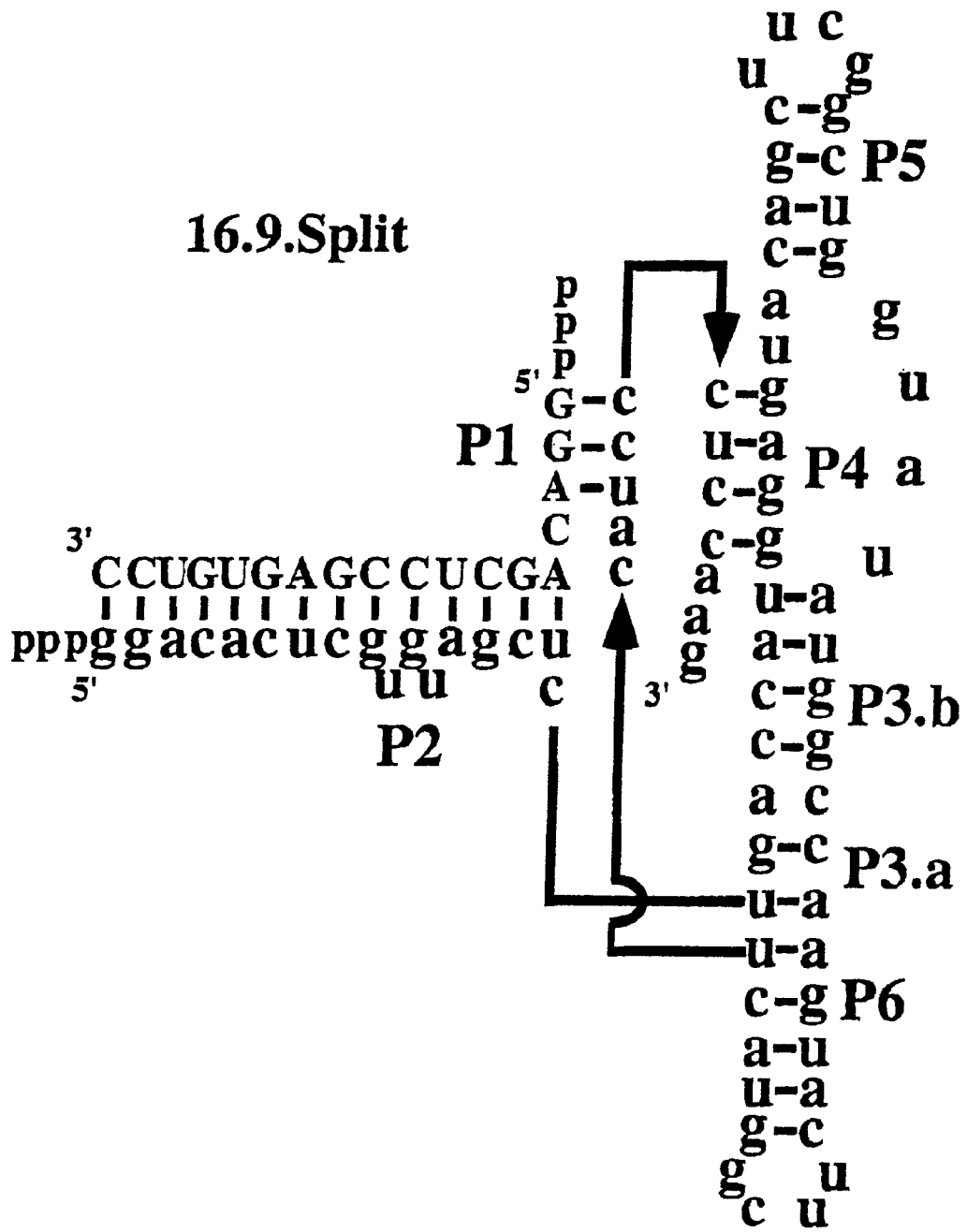
FIG. 6 is an example of a two-part ribozyme in which an 18-nt ribozyme segment (SEQ ID NO.: 7) is sufficient to specifically covalently link to the Tat tag peptide in the presence of the remainder of the ribozyme sequence. Also shown is the 79-nt ribozyme segment (SEQ ID NO.: 8) which is the second component of the two-part ribozyme. A model of the secondary structure of the two-part ribozyme is shown.

Isolated ribozymes of the present invention are catalytically active; they interact with and bind their respective peptide substrate(s), which in the embodiments described herein, act as peptide tags which, in effect, act as links between the components joined by the ribozyme's activity. Isolated ribozymes of the present invention can function as a single (contiguous) molecule or can occur as two ribozyme segments or components, which come together, join or interact, under the conditions used, to function as a complete ribozyme. The two components are one which comprises the ribozyme segment (or ribozyme RNA) which specifically interacts with (covalently links to) its peptide substrate and one which comprises the remainder of the ribozyme sequence. Ribozymes of this invention can comprise a motif or segment which specifically interacts with a peptide (its peptide substrate(s)) and is able to form a covalent bond with the peptide. For example, the isolated ribozymes represented schematically in FIG. 5A and FIG. 5B are specific examples of ribozymes of the present invention. Another example of an isolated ribozyme of the present invention, which is a two-part ribozyme, is represented in FIG. 6. The two-part ribozyme shown in FIG. 6 includes ribozyme RNA sufficient to covalently link to a peptide substrate. In this embodiment, the ribozyme RNA sufficient to covalently link to the peptide tag is 18 nucleotides and links to the Tat tag peptide or the Tat 2 tag peptide in the presence of the remainder of the ribozyme. In this embodiment, the remainder of the ribozyme is 79 nucleotides. It is to be understood that a wide variety of ribozymes and ribozyme segments or portions are useful in producing the encoded polypeptides and conjugates described herein. For example, sequences represented herein can be altered by replacing, deleting, substituting, adding and/or modifying one or more nucleotides to produce ribozymes/ribozyme segments which catalyze the same reaction (formation of a covalent bond with a peptide substrate). Altered sequences can be produced using known methods and then assessed for their catalytic activity, also using known methods. For example, the ribozyme sequences represented in FIG. 5A or FIG. 5B can be altered by replacing, deleting, substituting, adding and/or modifying at least one nucleotide, provided that they exhibit the ability to form a covalent link with a peptide substrate. Alteration can be extensive (e.g., 40% or more of the nucleotides can be altered). This is also the case for the two-part ribozyme represented in FIG. 6, provided that the altered form of the ribozyme RNA which specifically interacts with the peptide substrate retains or exhibits the ability to do so in the presence of the remainder of the ribozyme (which can be as shown in FIG. 6 or can itself also be altered in sequence). Alternatively, the sequence of the remainder of the ribozyme (e.g., the 79nt represented in FIG. 6 or another sequence) can be altered. Altered ribozymes and ribozyme segments can include modified or artificial/non-naturally occurring nucleotides.

Isolated ribozymes described herein are useful, for example, to join an mRNA to its translation product and, thus, to produce diverse libraries of encoded polypeptides, as well as to tag polypeptides with specific nucleic acids, to produce polypeptide-nucleic acid tag conjugates useful, for example, for detection, identification, separation, isolation or purification of the polypeptide and to change characteristics of the polypeptide.

Described herein and represented in the figures are embodiments of the present invention in which a ribozyme functions to join a polypeptide to a nucleic acid through or by means of specific interaction of the ribozyme with its substrate.

Generation of Diverse Libraries of Encoded Polypeptides

The present invention relates to a method of generating a diverse library or collection of encoded polypeptides; engineered mRNA from which the diverse libraries of encoded polypeptides are produced; isolated ribozymes which join an mRNA to its translation product; encoded polypeptide libraries generated by the method; polypeptide-engineered mRNA conjugates of which the diverse encoded polypeptide libraries are comprised; translation products of the engineered mRNAs; a method of identifying and, optionally, amplifying members of the encoded polypeptide library (referred to as target members) which have desired characteristics; target members of the library identified by the method; polypeptide fragments of the target members identified by this method; and ribonucleoprotein fragments of the target members identified by the method.

Engineered mRNA is used to produce a diverse encoded polypeptide library of the present invention; libraries of engineered mRNAs are one embodiment of this invention. Engineered mRNA comprises: (a) ribozyme RNA which specifically covalently links to a peptide; (b) a coding region for the peptide with which the ribozyme RNA specifically covalently links (the peptide tag); (c) a region which encodes a diverse polypeptide and (d) two PCR primer-binding sites. The ribozyme RNA segment which specifically covalently links to the peptide tag is present in (is part of) a ribozyme which occurs as a contiguous sequence or is comprised of two noncontiguous components: one which comprises the ribozyme RNA which specifically covalently links to the peptide tag and one which comprises the remainder of the ribozyme sequence. The two components join together, under the conditions used to produce diverse libraries, to form a complete ribozyme. The region which encodes a diverse polypeptide differs among engineered mRNAs, thus making it possible to produce a diverse encoded polypeptide library.

In addition to the elements described in the previous paragraph, engineered RNA can include one or more of the following optional components: three phosphate groups at the 5' end of the ribozyme RNA or an mRNA cap, such as a 7-methyl guanosine triphosphate; an RNA linker between the ribozyme sequence and the peptide tag coding region; a coding region for a peptide linker between the coding region for the peptide tag and the diverse coding region and a ribosomal stalling site between the diverse polypeptide segment and the second PCR primer-binding site.

The coding regions for the peptide tag, the optional peptide linker, and the diverse polypeptide segment are all fused in-frame so that they are translated as a single tripartite polypeptide. All components encoded by the engineered mRNA can be immediately adjacent to one another or can be separated from the preceding and/or following component (s) by an intervening amino acid residue or intervening amino acid residues. Similarly, components of the engineered mRNA can be separated by intervening nucleotides, provided that the components of the open reading frame remain in frame.

The ribozyme sequence of the engineered mRNA comprises a motif (a region) that interacts specifically with the peptide tag, with the result that polypeptide-engineered mRNA conjugates are produced. The ribozyme promotes the formation of a covalent bond between the ribozyme RNA (e.g., the 5'end) of the engineered message and a reactive group, such as a hydroxyl group or an amino group, of the peptide tag. The region coding for a peptide linker is an optional component of the engineered mRNA; however, if a peptide linker is to be produced, it must be of appropriate length (e.g., 2–10, 10–20, 15–25 or 20–30 amino acid residues and typically 30 amino acid residues or more) and composition to allow for presentation of the peptide tag for formation of the covalent bond. In an alternative embodiment, part (or all) of the ribozyme can reside within or downstream of the mRNA coding region. In another alternative embodiment, the peptide tag can be C-terminal of the diverse polypeptide segment and the engineered mRNA is designed accordingly.

In one embodiment, the engineered mRNA includes, in order (from the 5' end to the 3' end of the mRNA): a first PCR primer-binding site; a novel catalytic RNA (ribozyme) sequence, which may include or overlap with the PCR primer binding site; a coding region for a peptide tag which interacts specifically with a motif in the ribozyme sequence; optionally, a region coding for a peptide linker; a coding region (referred to as the diverse coding region) that differs among members of the library and encodes a polypeptide (referred to as the diverse polypeptide segment); and a second primer-binding site for reverse transcription and PCR amplification.

In a specific embodiment of the present invention, the engineered mRNA comprises (5'→3'): a novel ribozyme which comprises a motif, modified BIV-1 TAR RNA, which interacts specifically with the translated product of the second component of the engineered mRNA (such as that shown in FIG. 5), a peptide tag; a coding region for the peptide Tat tag (SEQ ID NO.: 1) or the Tat 2 tag peptide (SEQ ID NO.:2), which includes the BIV-1 (Bovine Immunodeficiency Virus-1) Tat peptide (SEQ ID NO.: 3); a coding region for a linker sequence of sufficient length (typically 30 amino acid residues or more) to allow presentation of the peptide tag to permit it to interact with the ribozyme; and a diverse coding region encoding the diverse polypeptide segment. In this embodiment, the engineered mRNA also comprises: a first PCR primer-binding site, located within the ribozyme sequence and overlapping the 5' portion of the modified BIV-1 TAR motif, and a second PCR primer-binding site, located 3' of the coding region.

Isolated ribozymes, which are catalytically active and assume a conformation which permits them to join or link an mRNA to the translation product of the mRNA, are also the subject of this invention. Such isolated ribozymes can be a contiguous molecule or can occur as two ribozyme segments or components, which can come together or interact to form the complete ribozyme. The two components are one which comprises the ribozyme RNA which specifically covalently links to the peptide tag and one which comprises the remainder of the ribozyme sequence. Isolated ribozymes of this invention comprise a motif which specifically interacts with a peptide and are able to form a covalent bond between themselves and the peptide. For example, when such isolated ribozymes are incorporated in (are a component of) an engineered mRNA of the present invention and the engineered mRNA undergoes translation as described herein, they join or link the engineered mRNA to its translation product by promoting formation of a covalent bond between the ribozyme RNA, the engineered message and a reactive group of the peptide tag encoded by the engineered mRNA.

Specific examples of isolated ribozymes are those represented by SEQ ID NO.: 5 and SEQ ID NO.: 6, which are represented schematically in FIGS. 5A and 5B. The conformations shown in FIGS. 5A and 5B are secondary structures it is reasonable to propose for the ribozyme of SEQ ID NO.: 5 and SEQ ID NO.: 6, respectively, but Applicants are not intending to be bound by this hypothesis. Another example of an isolated ribozyme is that represented in FIG. 6. This is an example of a two-part ribozyme, as described below. Other isolated ribozymes which comprise a nucleotide (RNA) sequence sufficiently similar to that of SEQ ID NO.: 5 or 6 and join an mRNA to the translation product of the mRNA, such as an isolated ribozyme which comprises a nucleotide sequence sufficiently similar to SEQ ID NO.: 5 or 6 that it results in the active (functional) conformation of the ribozyme of SEQ ID NO.: 5 or 6 (it has important secondary structural features assumed by the ribozyme of SEQ ID NO.: 5 or 6), are also the subject of this invention.

In another embodiment of the present invention, only a portion or segment (one or more nucleotides) of the ribozyme resides within the 5' untranslated region of the engineered mRNA; the remainder of the ribozyme resides elsewhere (e.g. within or downstream of the coding region, or on a separate RNA molecule). Although the parts or components of the ribozyme are not contained within a single contiguous sequence, they come together to form a ribozyme complex which is functionally equivalent to the ribozyme of the previously described embodiment (functionally equivalent to a complete ribozyme). For example, one or more nucleotides (e.g., the first nucleotide, the first 13, 14, 15, 16, 17 or 18 nucleotides of the ribozyme, or more) are at the 5' end of the engineered mRNA; the remaining residues are supplied as a separate RNA molecule such that a ribozyme complex is formed and binds the tag peptide and covalently joins the ribozyme portion or segment to the peptide tag. As used herein, the term "ribozyme RNA" includes ribozymes, ribozyme portions and ribozyme segments.

In an example of this embodiment, pppGGA, the first three residues of the ribozyme shown in FIG. 5 (SEQ ID NO.: 5), resides at the 5' end of the engineered mRNA and the remaining ribozyme residues are supplied as a separate RNA molecule such that a ribozyme complex is formed that binds the Tat tag peptide and covalently joins the GGA ribozyme segment to the peptide tag. In a further example of this embodiment, as many as the first 18 residues of the ribozyme shown in FIG. 5 (e.g., from residues 1 to 18 and any shorter portions such as the first 13, 14, 15, 16 or 17 residues) reside at the 5' end of the engineered mRNA, and the remaining ribozyme residues are supplied as a separate RNA molecule such that the two components form a ribozyme complex (complete ribozyme) that binds the Tat tag peptide and covalently joins the ribozyme segment to the peptide tag. One example of an 18 nucleotide (nt) ribozyme RNA segment (GGACAGCUCCGAGUGUCC; SEQ ID NO.: 7) that specifically covalently links to the Tat tag peptide in the presence of the remainder of the ribozyme sequence is shown in FIG. 6. In another embodiment, the ribozyme RNA that specifically covalently links with a peptide is at least 18 nucleotides of a ribozyme or is a contiguous sequence.

In the method of generating libraries of encoded polypeptides, engineered mRNAs and sufficient in vitro translation mixture are combined to produce a combination of the two and the combination is maintained under conditions appropriate for translation of the engineered mRNAs (and, thus, expression of the product encoded by the engineered mRNAs) to occur. In one embodiment, a library of encoded polypeptides is produced by combining an in vitro translation mixture derived from rabbit reticulocytes and a library of engineered mRNAs, described herein, in which a ribozyme (such as that shown in FIG. 5) includes a modified BIV-1 TAR RNA motif and in which the coding region for a peptide tag encodes the peptide Tat tag peptide (SEQ ID NO.: 1). The in vitro translation mixture is a combination of biological reagents and cellular components which translates the engineered mRNA to produce the polypeptide product it encodes. In vitro translation mixtures from E. coli, wheat germ and rabbit reticulocytes are commercially available from Promega.

When the in vitro translation mixture and a library of engineered mRNA are combined and maintained under appropriate conditions, translation is initiated at the start codon (e.g., AUG) of the engineered mRNA and proceeds 5'→3'. The peptide tag is produced, followed by the linker, if one is encoded by the engineered mRNA. After the peptide tag emerges from a translating ribosomal complex, the ribozyme interacts with the peptide tag and promotes formation of a covalent linkage between the ribozyme RNA of the message and a reactive group, such as a hydroxyl group or an amino group, of the peptide tag. If a linker is encoded by the engineered mRNA, the linker permits the peptide tag to be presented in such a manner that the reactive group of the peptide tag is available for formation of the covalent linkage with the 5' end of the engineered mRNA. Translation of the diverse coding region can occur before, during, or after the covalent linkage of the peptide tag and an engineered mRNA. As a result, the newly-produced polypeptide is covalently linked to the engineered mRNA that encodes it.

Encoded polypeptides produced by the method described herein and libraries of encoded polypeptides are also the subject of this invention. The encoded polypeptides are conjugates which each, in turn, comprise an engineered mRNA, linked to its translation product by a covalent bond between the 5' end of the engineered mRNA and a reactive group, such as a hydroxyl group or an amino group, of the peptide tag (the ribozyme substrate). The translation product of an engineered mRNA comprises the peptide tag and the diverse polypeptide segment and, optionally, the linker sequence. If a linker sequence is present, the term translation product refers to these three components. Translation products are also the subject of this invention.

Thus, encoded polypeptides of the present invention, which are described above with reference to the engineered mRNAs which encode them, each comprise an engineered mRNA and its translation product, joined by a covalent bond between the ribozyme RNA of the engineered mRNA and a component of the translation product (the peptide tag). The peptide tag can be any peptide of appropriate composition and length to result in specific interaction between itself and the ribozyme sequence. In one embodiment, the peptide tag is the Tat tag peptide (SEQ ID NO.: 1), which includes the BIV-1 Tat peptide. Alternatively, the peptide tag is the Tat 2 tag peptide (SEQ ID NO.:2).

The optional peptide linker is of sufficient length and composition for it to present the peptide tag for formation of a covalent bond between a reactive group of the tag and the ribozyme RNA of the engineered mRNA. That is, the peptide tag and the ribozyme RNA of the engineered mRNA must come together such that the covalent bond is formed.

The diverse polypeptide segment can be a polypeptide of any length and can be encoded by mRNA sequences which occur in nature (such as in a library which represents the mRNA or DNA sequences present in cells) or is produced chemically. For example, the mRNA or DNA present in prokaryotic or eukaryotic cells (including invertebrate and vertebrate cells, including mammalian, such as human cells) can be used to produce a library of engineered mRNAs, which, by in vitro translation, result in production of a library of encoded polypeptides in which the diverse polypeptide segments represent the population of polypeptides expressed in the cells. Alternatively, randomly-produced mRNA, such as that produced by combinatorial chemical synthesis to produce mRNAs or by transcribing DNAs produced by combinatorial chemical synthesis of DNA, can be used to make engineered mRNA libraries.

The components of the translation product can be immediately adjacent to one another or can be separated by one or more intervening amino acid residues (amino acid residues which are not members of the peptide tag, peptide linker or diverse polypeptide segment).

In one embodiment, a diverse library of encoded polypeptides is comprised of conjugates of an engineered mRNA and its translation product in which the ribozyme, such as that shown in FIG. 5, includes a modified BIV-1 TAR RNA motif (SEQ ID NO.:3) and the coding region for a peptide tag encodes the Tat tag peptide (SEQ ID NO.: 1) or the BIV-1 Tat 2 tag peptide (SEQ ID NO.: 2).

Once a diverse encoded polypeptide library has been produced, it can be screened, using known methods, to identify target members which are conjugates with desired characteristics. A key advantage of the diverse encoded polypeptide library of the present invention, which is comprised of polypeptide-engineered mRNA conjugates, is that even members which occur in small numbers (rare members) and are of interest because of desired biological or biochemical properties (e.g., binding to a particular ligand, enzymatic activity) can be enriched and then identified by amplification, cloning and sequencing of their respective mRNAs.

A diverse library of encoded polypeptides can be enriched in target members, using known methods. Methods by which target members of the library can be enriched and identified include affinity enrichment using immobilized ligand or binding partner and, for enzymatic activity, affinity to a product of a reaction in which the enzyme has modified itself (with, for example, a mechanism-based inhibitor) or a substrate to which it is attached (see, e.g., Williams, K. P. and D. P. Bartel, "In Vitro Selection of Catalytic RNA", pp. 367–381 In: *Catalytic RNA,* (Fritz Eckstein and David M. J. Lilley, Ed.), Springer (1996)).

Furthermore, libraries enriched in target members can be amplified and subjected to additional enrichment and amplification. For example, a library of conjugates that has been enriched for a desired activity (an enriched encoded polypeptide library) can be reverse transcribed, producing the cDNA of the mRNA components. The cDNAs can then be amplified (e.g., by PCR or other amplification methods). The resulting PCR products are subjected to in vitro transcription, resulting in production of an amplified pool of engineered mRNAs of the enriched conjugate library. In vitro translation of this pool results in linking of the mRNA to its translation product, producing an amplified version of the enriched encoded polypeptide library. Conjugates amplified in this way are subjected to further enrichment and amplification, which is repeated as necessary until target members are enriched to the desired extent (e.g., enriched to a level where they are present in sufficient numbers to be detected by binding to a ligand of interest, or catalyzing a reaction of interest). After sufficient enrichment, mRNA target members are cloned and individual conjugates can be screened for the desired function. The translation product of the mRNA or a fragment of the translation product (particularly, the diverse polypeptide segment) can also be screened for activity without attachment to the engineered mRNA. One embodiment of the present method of identifying members of a diverse encoded polypeptide library which exhibit a desired activity or characteristic (target members) comprises the steps of:

(a) producing a diverse encoded polypeptide library which comprises polypeptide-engineered mRNA conjugates by:
  (i) combining:
    (1) a library of engineered mRNAs, each of which comprises, in order (from the 5' end of the mRNA to the 3' end of the mRNA): a) a ribozyme sequence which comprises a first PCR primer—binding site and a motif that interacts specifically with a peptide; b) a coding region for the peptide (referred to as a peptide tag) with which the motif of the ribozyme sequence interacts specifically; c) a region coding for a linker sequence; d) a coding region for a diverse polypeptide segment; and e) a second PCR primer-binding site and
    (2) an appropriate in vitro translation mixture, with the result that a combination is produced;
  (ii) maintaining the combination under conditions appropriate for translation of the engineered mRNA to occur, whereby the translation product of the engineered mRNA (which comprises the peptide tag, the linker sequence and the diverse polypeptide segment) is produced and joined to the engineered mRNA by a covalent bond between the 5' end of the engineered mRNA and a reactive group of the peptide tag, thereby producing polypeptide-engineered mRNA conjugates;

(b) enriching the diverse encoded polypeptide library for members which exhibit a desired activity, thereby producing an enriched polypeptide library comprised of polypeptide-engineered mRNA conjugates;

(c) amplifying the enriched polypeptide library by:
  (i) reverse transcribing the engineered mRNA component of the conjugates, thereby producing the corresponding cDNA,
  (ii) amplifying and transcribing in vitro the corresponding cDNA, thereby producing a pool of amplified, enriched engineered mRNA;
  (iii) combining the pool of amplified, enriched engineered mRNA with an appropriate in vitro translation mixture, thereby producing a combination;
  (iv) maintaining the combination under conditions appropriate for translation of the engineered mRNA to occur, whereby the translation product of the engineered mRNA is produced and joined to the engineered mRNA by a covalent bond between the 5' end of the engineered mRNA and a reactive group of the peptide tag, thereby producing an amplified enriched polypeptide library comprised of polypeptide-engineered mRNA conjugates;

(d) repeating steps b) and c), as necessary, until members which exhibit the desired activity are present in sufficient number to be detected; and (e) detecting members which exhibit the desired activity, thereby identifying members which exhibit the desired activity. In one embodiment of the method, the ribozyme sequence comprises SEQ ID NO.: 5. In another, the motif that interacts specifically with a peptide is modified BIV-1 TAR RNA and the peptide tag is the Tat tag or the Tat 2 tag peptide; the ribozyme sequence in this embodiment can comprise SEQ ID NO.: 5. In the method, the region coding for a linker sequence encodes a linker of appropriate length, as described previously; typically it encodes a linker of 30 amino acid residues or more, although a shorter linker (e.g., 10 or more amino acid residues) can be used.

The translation products of the enriched mRNA (the polypeptide component of the target members), such as polypeptides which display activities of interest (e.g., ligand binding or catalytic activity) as well as engineered derivatives of these translation products which display activities of interest are referred to as target polypeptide fragments. These target polypeptide fragments are also the subject of this invention. Target polypeptide fragments can be released or separated from target members in which they occur, using known methods (e.g., RNA), or they can be synthesized without attachment to the mRNA (e.g., using chemical synthesis or mRNA translation in the absence of the tRNA analogue. They can be used, for example, as diagnostic or therapeutic reagents, (e.g., single-chain monoclonal antibodies), protein catalysts, members of binding pairs, receptors or their ligands, enzymes or enzyme substrates. Once a polypeptide fragment which has desired characteristics has been identified, it can be produced using known methods (e.g., production in an appropriate expression system, chemical synthesis).

Ribonucleoprotein fragments of the target members are also the subject of this invention. They can be used, for example, as enzymes or ligands.

The present invention will now be illustrated by the following examples, which are not intended to be limiting in any way.

Tagging Polypeptides with Nucleic Acids

Purification or detection of nucleic acids is typically more facile than is purification or detection of proteins. This is an inherent advantage of nucleic acids, which results from the predictable hybridization properties of nucleic acid target sequences. Nucleic acids with high affinity and specificity for the target sequence(s) can readily be designed and synthesized. In addition, large numbers of nucleic acid sequences can be analyzed in parallel using, for example, hybridization to DNA chips. In contrast, detecting a particular protein target often requires investing considerable effort in generating antibodies or aptamers that specifically recognize the target protein. Although this difficulty in detecting and purifying can be overcome for recombinant proteins by using affinity tag fusions, the parallel detection of large numbers of different recombinant proteins is limited by the small repertoire of affinity tags, as well as distinct—and sometimes incompatable—incubation protocols for each tag. This limitation can be overcome by attaching nucleic acid tags to polypeptides (also referred to as proteins); as described herein, tagging polypeptides is accomplished through the activity of isolated ribozymes of the present invention, which specifically recognize and bind to a peptide substrate(s). Polypeptides tagged with a specific or selected nucleic acid (RNA or DNA) are referred to herein as polypeptide-nucleic acid tag conjugates and comprise: a polypeptide of interest (or target polypeptide); a peptide substrate of the ribozyme used to join the polypeptide and the nucleic acid components (also referred to as a peptide tag); ribozyme RNA and a nucleic acid tag. Polypeptide-nucleic acid conjugates, methods of producing the conjugates, methods of using the conjugates are also the subject of this invention.

Figure 8A:
FIGS. 8A–8C represent schematically a second embodiment of the invention, by which polypeptide-nucleic acid tag conjugates are produced.
Figure 8A:
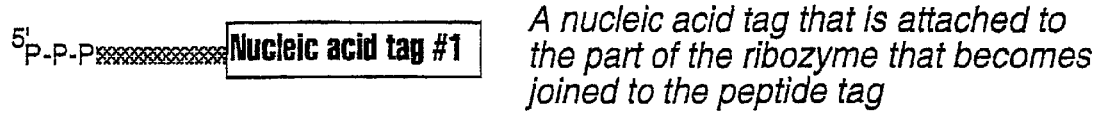
Figure 8A:
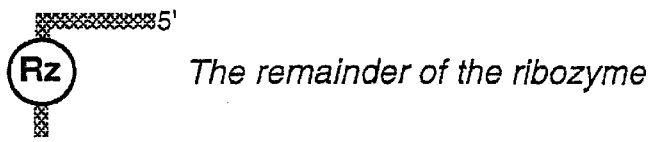
Figure 8B:
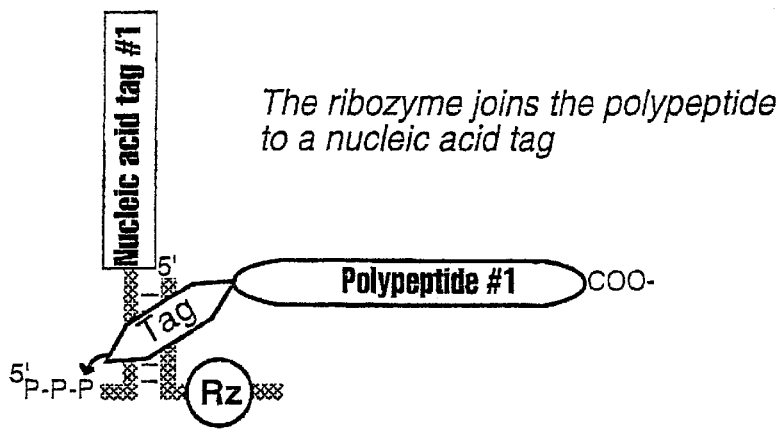
Figure 8C:
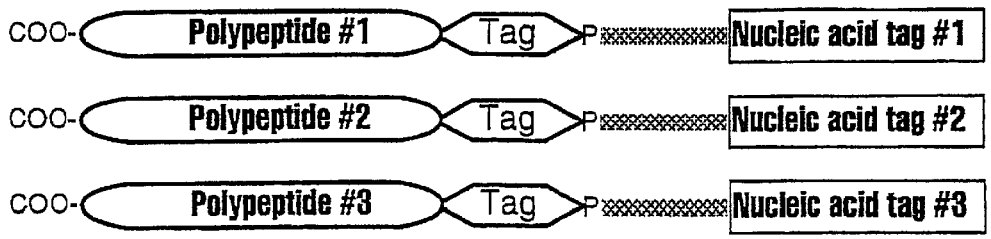

Polypeptide-nucleic acid tag conjugates are produced as follows: A polypeptide of interest which is fused with a peptide tag which is a substrate of the ribozyme is combined with (a) ribozyme RNA which specifically covalently links to the peptide tag and has linked thereto or bears a nucleic acid tag and (b) additional ribozyme RNA which, in combination with segment bearing the nucleic acid tag forms a complete/functional ribozyme, under conditions appropriate for the ribozyme RNA of (a) to specifically covalently link to the peptide tag. As a result, the polypeptide of interest is tagged with the nucleic acid tag. Alternatively, a complete ribozyme bearing a nucleic acid tag is combined with the polypeptide of interest bearing the peptide tag (ribozyme substrate). For example, a polypeptide of interest which is fused at its amino terminus with a peptide tag which is a peptide substrate of the ribozyme to be used is combined with: (a) the ribozyme, which bears or is joined with a specific nucleic acid sequence (the nucleic acid tag), or (b) segments of a ribozyme, wherein one ribozyme segment is joined at its 3' end with a nucleic acid sequence and in the presence of a second ribozyme segment forms a covalent bond with the amino terminus of the peptide tag under conditions appropriate for the ribozyme RNA to specifically interact with its peptide substrate (the peptide tag present on the polypeptide of interest). As a result, the ribozyme or ribozyme segment (which bears the specific nucleic acid sequence) interacts specifically with the peptide tag of the polypeptide of interest, forming a covalent link or bond and, thus, tagging the polypeptide of interest with the specific nucleic acid. FIGS. 8A–8C represent a specific embodiment of this process schematically. In the embodiment represented in FIG. 8A, a polypeptide is tagged at its amino terminus with a peptide tag which is a substrate for the ribozyme to be used in producing polypeptide-nucleic acid conjugates. The peptide tag is joined or linked to the amino terminus of the polypeptide using known recombinant methods. The polypeptide can be any polypeptide it is desired to detect, identify, isolate, purify or alter in terms of its characteristics (e.g., solubility, size, functions, intracellular location). It can be of any length and can be present, for example, in a body fluid or tissue, cell lysate, food product, beverage, water, or library of proteins. Also shown in the example as represented in FIG. 8A, the ribozyme to be used can comprise two components: a first region, which recognizes or becomes joined to the peptide tag on the polypeptide, which bears the nucleic acid tag at its 3' end and a second region, which is the remainder of the ribozyme (which, when interacting with the first ribozyme component, forms a complete/functional ribozyme). In FIG. 8A, P-P-P represents the 5' triphosphate of the ribozyme of the specific embodiment shown.

As shown in FIG. 8B, when the three entities represented in FIG. 8A are combined under appropriate conditions (e.g., 1 hr. in 100 mM KOAc, 50 mM Tris-OAc pH7.5, 30 mM NH$_4$OAc, 15 mM Mg(OAc)$_2$, 2 mM DTT, a functional ribozyme is formed and the polypeptide is joined to the nucleic acid tag through the interaction of the ribozyme (which bears the nucleic acid tag) with the peptide tag (ribozyme substrate). In a specific embodiment, in which the two-part ribozyme represented in FIG. 6 is used, the covalent linkage is formed by attack of the amino terminus of the peptide tag on the 5' triphosphate of the ribozyme, as indicated by the arrow in FIG. 8B. FIG. 8C is a schematic representation of resulting polypeptide-nucleic acid tag conjugates, which comprise the polypeptide of interest, the peptide tag (present at the amino terminus of the polypeptide), the ribozyme covalently joined to the peptide tag and the nucleic acid tag. As discussed above, the variety of nucleic acid tags is unlimited and, thus, an unlimited number of polypeptides can be tagged with a specific (different) nucleic acid.

The ribozymes described above can be used for generating the polypeptide-nucleic acid tag conjugates of this invention. The nucleic acid tags can be any sequence of nucleotides and can be DNA, RNA, PNA or any other type of modified nucleic acid. They can be made using known methods and can be of any length, provided that the tag remains hybridized with its complement (binding partner) under the conditions used. They will generally be at least 10 nucleic acids in length and range from 4 to 30 or more nucleic acids in length.

Polypeptide-nucleic acid tag conjugates have a wide variety of uses, which encompass essentially any context in which separation, isolation, purification, detection or identification of a recombinant polypeptide is desired and/or in which alteration of a characteristic(s) of the polypeptide is desired. For example, in one embodiment, polypeptides in a cell lysate are tagged, as described herein, with a nucleic acid. Each polypeptide is preferably tagged with a different nucleic acid, with the result that each polypeptide is in essence uniquely tagged. The complementary sequence of a nucleic acid tag is used as a binding partner for the tag and, in one embodiment, is bound to a solid surface. Hybridization of the nucleic acid tag of the conjugate with its complement results in attachment of the complex to a solid surface (e.g., beads, chip or other planar surface, wells, columns) if the complement is bound to a solid surface and remains bound under the conditions used. Alternatively, the binding partner can be in solution or suspension and hybridization, thus, occurs in the solution or suspension. The binding partner can be totally complementary to the nucleic acid tag or can be less than totally complementary in sequence, provided that the nucleic acid tag of the conjugate remains bound (hybridized) to the binding partner nucleic acid under the conditions used. Subsequently, the polypeptide-nucleic acid tag conjugate can be released from the binding partner by changing conditions such that hybridization no longer occurs (e.g., by lowering ionic strength.). The polypeptide can be separated from the complex, for example, for characterization (such as sequencing or structural assessments, modification or determination of biological activity/function) using known methods (e.g., nuclease treatment). Polypeptides obtained in this way are useful as drugs, drug targets, and diagnostic reagents.

Alternatively, polypeptide-nucleic acid tag conjugates can be formed in order to alter a characteristic or characteristics of polypeptides. For example, solubility of polypeptides can be altered [reduced or enhanced] in this manner. Increasing the solubility of an expressed protein by adding a nucleic acid tag can prevent aggregation during protein purification without disrupting the native fold of the protein. Activity of a polypeptide can also be altered, making it possible to express levels of the protein that would otherwise be toxic. Mobility of a polypeptide can be altered by tagging with a nucleic acid, providing a means by which polypeptides in a mixture can be separated from one another, using, for example, gel electrophoresis. The invention is illustrated by the following examples, which are not intended to be limiting in any way.

EXEMPLIFICATIONS

Example 1
A Ribozyme That Links a Peptide Tag to Itself

This ribozyme has the sequence:
GGACAGCUCCGAGCAUUCUCGUGUAGCU-
CUGACCAUGGAGUACAGCACCA
CGUCGUCGCUGGUAUAUGGC-
CAAGUAAUAAACGACUCAUCCCUCCAAG (SEQ ID NO.: 5)

Without wishing to be bound by theory, the ribozyme is predicted to fold into the secondary structure shown in FIG. 5. In FIG. 5, the modified TAR motif is indicated (uppercase).

Figure 4:
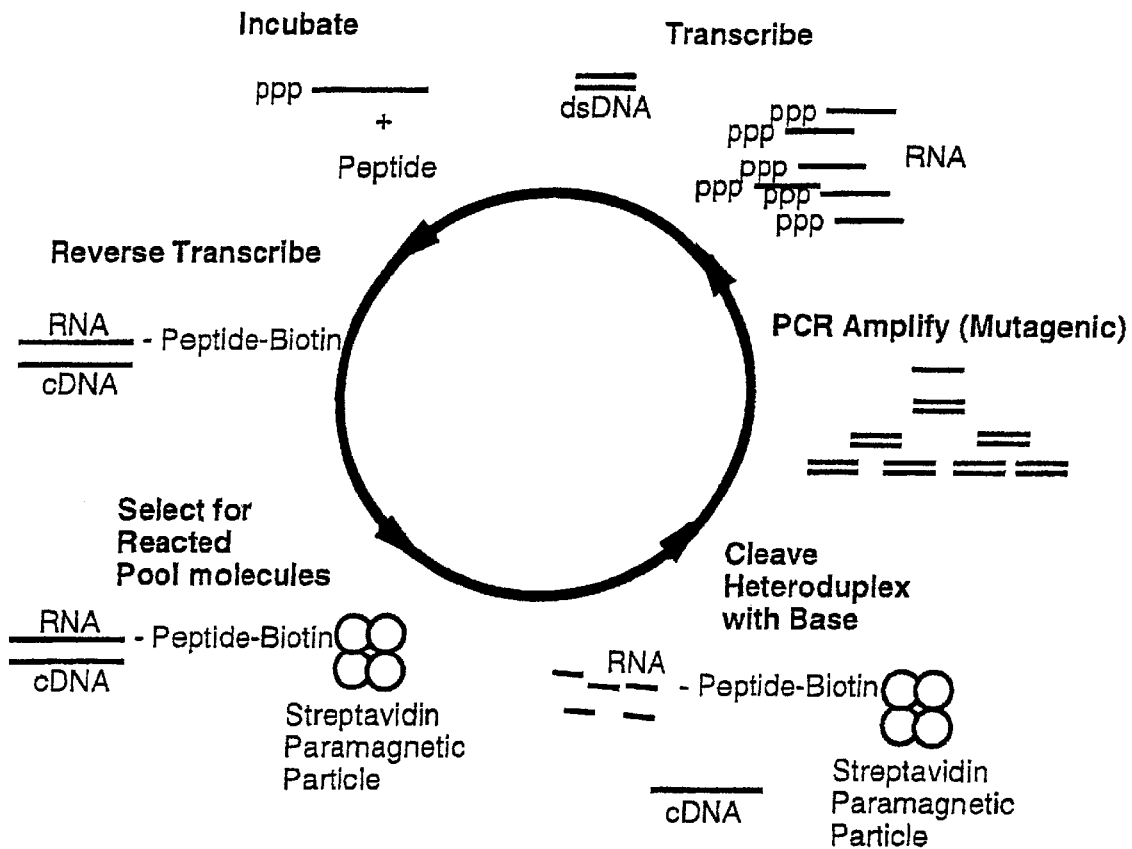
FIG. 4 is a schematic representation of a ribozyme selection procedure.

The 5' ribozyme activity was isolated from a large population of >$10^{14}$ randomized RNA molecules following the procedure outlined below and represented in FIG. 4.
1) In vitro transcribed RNA was incubated overnight with a biotinylated Tat tag peptide (MSYSGPRPRGTRGKGRRIRRGGK-BIOTIN).
2) The RNA population was reverse transcribed to generate an RNA-cDNA heteroduplex.
3) Ribozyme molecules that joined themselves to the biotinylated peptide were separated from unreacted molecules by incubating the heteroduplex with paramagnetic particles coated with Streptavidin.
4) The RNA strand of the heteroduplex was cleaved with alkali to free the DNA copy of the RNA from the support.
5) This DNA was amplified using PCR.
6) The resulting double-stranded DNA was then used as template in an in vitro transcription reaction to generate a new population of RNA molecules. Repeating steps 1–6 selectively enriched for ribozymes that can covalently attach themselves to the modified BIV-1 peptide.

Example 2
An 18-nt Ribozyme RNA Segment that Specifically Covalently Links to the Tat Tag Peptide in the Presence of the Remainder of the Ribozyme Sequence 16.9.split (FIG. 6) is a two-part ribozyme that is a version of the ribozyme shown in FIG. 5A (SEQ ID NO: 5), where the ribozyme has been split at the loop of paired-region 2 (P2) and the P2 helix has been extended by 5 base pairs. The loops of P5 and P6 have also been shortened and stabalized. This 18-nt RNA (SEQ ID NO: 7, pppGGACAGCUCCGAGUGUCC) and 79-nt RNA (SEQ ID NO. 8, pppGGACACUCGUGUAGCUCUGACCAUG-GAGUACAGCUUCGGCUGGUAUA UGGCCAAGUACUUCGGUACUCAUCCCUCCAAG) function together as a ribozyme in which the 18-nt ribozyme RNA segment specifically covalently links to the Tat tag peptide.

Figure 1:
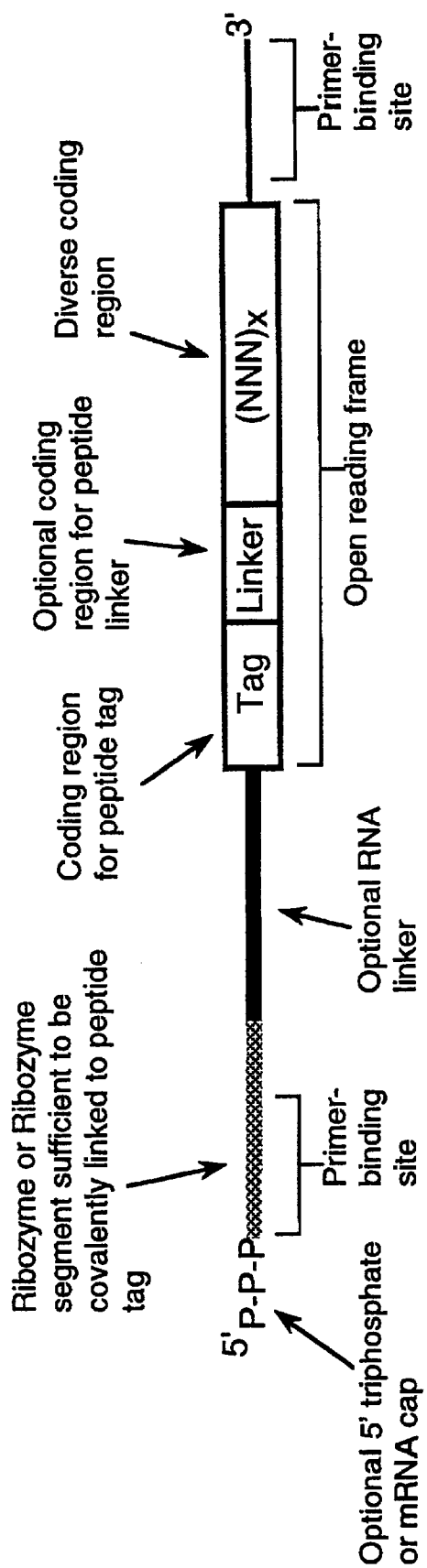
FIG. 1 is a schematic representation of an engineered mRNA. P-P-P represents the 5' triphosphate of the engineered mRNA. This triphosphate can be modified or replaced to facilitate linkage to the translation product or to enhance the efficiency of in vitro translation; for example, a 7-methyl guanosine cap can be used to increase the efficiency of translation in eucaryotic translation extracts (e.g., those from wheat germ extract or rabbit reticulocytes).
Figure 2:
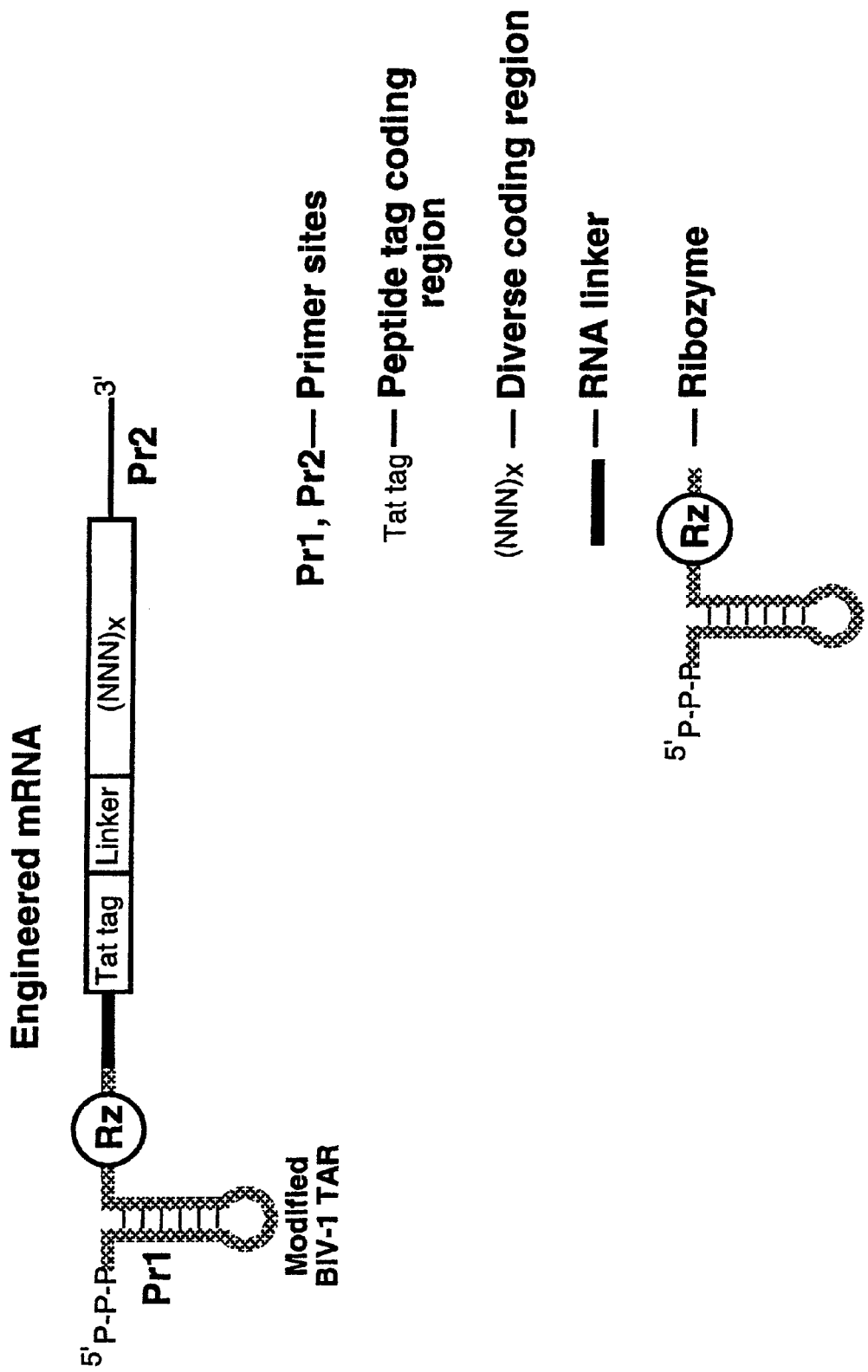
FIG. 2 is a schematic representation of an engineered mRNA in which the ribozyme sequence includes a modified BIV-1 TAR RNA motif and the coding region for a peptide tag encodes the Tat tag peptide (SEQ ID NO.: 1), or the Tat 2 tag peptide (SEQ ID NO.: 2) where Tat is the BIV-1 Tat peptide (SEQ ID NO.: 3).
Figure 7:
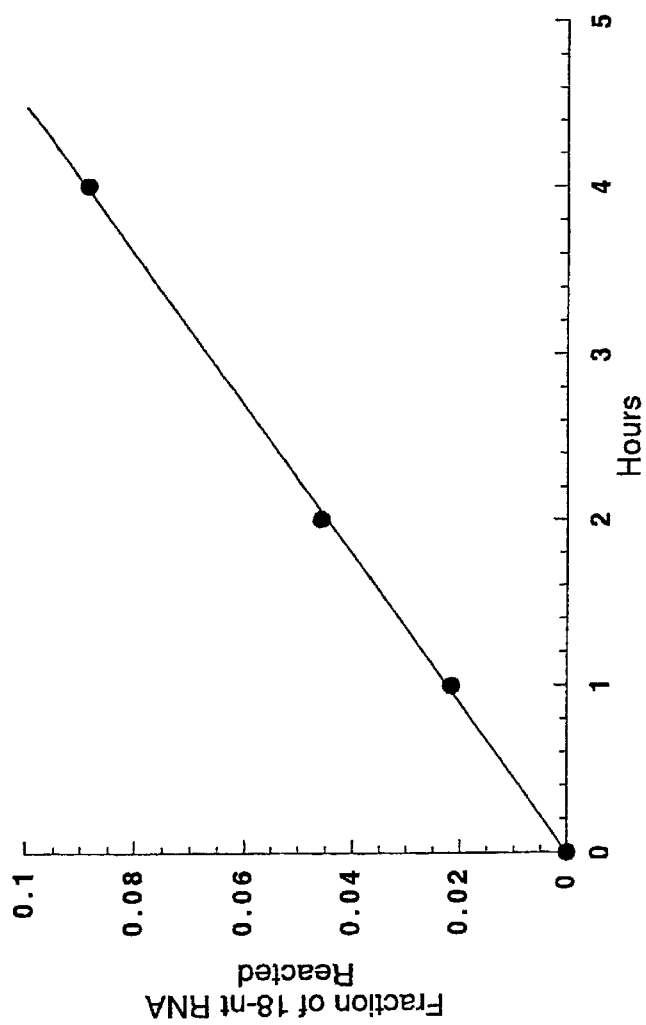
FIG. 7 is a graphic representation of results of analysis, using a phosphorimager, of accumulation of the product of incubation of the two-part ribozyme shown in FIG. 6 with biotinylated Tat tag peptide.
Figure 3D:

The two ribozyme RNAs of 16.9.split (SEQ ID NO: 7 and 8) shown in FIG. 6 were transcribed in vitro using T7 RNA polymerase and appropriate templates. The RNAs were gel purified, then incubated together with biotinylated Tat tag peptide (SEQ ID NO.1) in reaction buffer 1.2 µM radiolabeled SEQ ID NO 4, 3.3 µM SEQ ID NO. 7, 1 mM Tat tag peptide, 100 mM KOAc, 50 mM Tris-OAc pH 7.5, 30 mM $NH_4OAc$, 15 mM $Mg(OAc)_2$, 2mM DTT). Aliquots were taken at 0, 1,2, and 4 hours and the accumulation of product observed as a shifted product on a 15% polyacrylamide/8M urea denaturing gel. The gel was analyzed using a phosphorimager and the fraction of labeled 18 nt ribozyme RNA that had been linked to the peptide was determined (FIG. 7).

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain, using no more than routine experimentation, many equivalents to the specific embodiments of the invention described specifically herein. Such equivalents are intended to be encompassed in the scope of the claims.

---

We claim:

1. Engineered mRNA which comprises:
   (a) ribozyme RNA which specifically covalently links to a peptide in the presence of the remainder of the ribozyme;
   (b) a coding region for the peptide with which the ribozyme RNA of (a) specifically covalently links, wherein the peptide is referred to as a peptide tag;
   (c) a coding region for a diverse polypeptide; and
   (d) two PCR primer-binding sites.

2. The engineered mRNA of claim 1 wherein the ribozyme RNA of (a) is one nucleotide.

3. The engineered mRNA of claim 2 wherein the ribozyme RNA of (a) is guanosine triphosphate.

4. The engineered mRNA of claim 1 wherein the ribozyme RNA of (a) is from 1 to about 18 nucleotide residues, inclusive, wherein the 1 to 18 nucleotide residues are from the 5' end of the ribozyme sequence.

5. The engineered mRNA of claim 1 wherein the ribozyme of (a) comprises at least 18 nucleotides.

6. The engineered mRNA of claim 1 wherein the ribozyme RNA of (a) is a contiguous sequence.

7. The engineered mRNA of claim 1 wherein the ribozyme comprises modified BIV-1 TAR RNA and the peptide tag is the Tat tag peptide or the Tat 2 tag peptide.

8. The engineered mRNA of claim 1 which further comprises a coding region for a peptide linker, wherein the coding region for the peptide linker is located between (b) and (c).

9. The engineered mRNA of claim 8 wherein the region coding for a linker sequence encodes a linker of 30 amino acid residues or more.

10. The engineered mRNA of claim 1 which further comprises a ribosome stalling site located between the coding region for a diverse polypeptide and the second PCR primer-binding site.

11. The engineered mRNA of claim 1 wherein the ribozyme is the ribozyme of SEQ. ID NO.: 5 or SEQ ID NO.:6.

12. A library of engineered mRNAs wherein each engineered mRNA in the library comprises:
   (a) ribozyme RNA which specifically covalently links to a peptide in the presence of the remainder of the ribozyme;
   (b) a coding region for the peptide with which the ribozyme RNA of (a) specifically covalently links, wherein the peptide is referred to as a peptide tag;
   (c) a coding region for a diverse polypeptide segment; and
   (d) two PCR primer-binding sites.

13. The library of claim 12 wherein the ribozyme RNA of (a) is one nucleotide.

14. The library of claim 13 wherein the ribozyme RNA of (a) is guanosine triphosphate.

15. The library of claim 12 wherein the ribozyme RNA of (a) is from 1 to about 18 nucleotide residues, inclusive, wherein the 1 to about 18 nucleotides are from the 5' end of the ribozyme sequence.

16. The library of claim 12 wherein the ribozyme RNA of (a) comprises at least 18 nucleotides.

17. The library of claim 12 wherein the ribozyme RNA of (a) is a contiguous sequence.

18. The library of claim 12 wherein the ribozyme RNA comprises modified BIV-1 TAR RNA and the peptide tag is the Tat tag peptide or the Tat 2 tag peptide.

19. The library of claim 12 wherein each engineered mRNA additionally comprises a coding region for a peptide linker, wherein the coding region for the peptide linker is located between (b) and (c).

20. The library of claim 19 wherein the region coding for a peptide linker encodes a linker of 30 amino acid residues or more.

21. The library of claim 12 wherein the engineered mRNA further comprises a ribosome stalling site located between the coding region for a diverse polypeptide and the second PCR primer-binding site.

22. The library of claim 12 wherein in each engineered mRNA the ribozyme RNA is the ribozyme of SEQ. ID No.: 5 or SEQ ID NO.: 6.

23. A polypeptide-engineered mRNA conjugate comprising:
   (a) an engineered mRNA which comprises:
      (1) ribozyme RNA which specifically covalently links to a peptide in the presence of the remainder of the ribozyme;
      (2) a coding region for the peptide with which the ribozyme RNA of (a) covalently links, wherein the peptide is referred to as a peptide tag;
      (3) a coding region for a diverse polypeptide; and
      (4) two PCR primer-binding sites; and
   (b) the translation product of the engineered mRNA, which comprises the diverse polypeptide and the peptide tag,
wherein the ribozyme RNA of the engineered mRNA is joined to the peptide tag by a covalent bond between the ribozyme RNA of the engineered mRNA and a reactive group of the peptide tag.

24. The polypeptide-engineered mRNA conjugate of claim 23 wherein the ribozyme RNA of (a) is one nucleotide.

25. The polypeptide-engineered mRNA conjugate of claim 23 wherein the ribozyme RNA of (a) is from 1 to about 18 nucleotide residues, inclusive, wherein the 1 to about 18 nucleotides are from the 5' end of the ribozyme sequence.

26. The polypeptide-engineered mRNA conjugate of claim 23 wherein the ribozyme RNA of (a)(1) comprises at least 18 nucleotides.

27. The polypeptide-engineered mRNA conjugate of claim 23 wherein the ribozyme of (a)(1) is a contiguous sequence.

28. The polypeptide-engineered mRNA conjugate of claim 23 wherein the ribozyme RNA of (a)(1) comprises modified BIV-1 TAR RNA and the peptide tag is the Tat tag peptide or the Tat 2 tag peptide.

29. The polypeptide-engineered mRNA conjugate of claim 23 wherein each engineered mRNA additionally comprises a coding region for a peptide linker, wherein the coding region for the peptide linker is located between (a)(2) and (a)(3).

30. The polypeptide-engineered mRNA conjugate of claim 29 wherein the region coding for a peptide linker encodes a linker of 30 amino acid residues or more.

31. The polypeptide-engineered mRNA conjugate of claim 23 wherein the engineered mRNA further comprises a ribosome stalling site located between the coding region for a diverse polypeptide and the second PCR primer-binding site.

32. The polypeptide-engineered mRNA conjugate of claim 23 wherein in each engineered mRNA the ribozyme RNA is the ribozyme of SEQ. ID No.: 5 or SEQ ID NO. 6.

33. A diverse encoded polypeptide library comprised of polypeptide-engineered mRNA conjugates, wherein each encoded polypeptide-engineered mRNA conjugate in the library comprises:
  (a) an engineered mRNA which comprises:
    (1) ribozyme RNA which specifically covalently links to a peptide in the presence of the remainder of the ribozyme;
    (2) a coding region for the peptide with which the ribozyme RNA of (a) specifically covalently links, wherein the peptide is referred to as a peptide tag;
    (3) a coding region which encodes a polypeptide to be expressed; and
    (4) a second PCR primer-binding site; and
  (b) the translation product of the engineered mRNA, which comprises the polypeptide to be expressed and the peptide tag,
wherein the ribozyme RNA of the engineered mRNA is joined to the peptide tag by a covalent bond between the ribozyme RNA of the engineered mRNA and a reactive group of the peptide tag.

34. The diverse encoded polypeptide library of claim 33 wherein in each engineered mRNA the ribozyme RNA is the ribozyme of SEQ ID NO.: 5 or SEQ ID NO.: 6.

35. The diverse encoded polypeptide library of claim 33 wherein the engineered mRNA further comprises a coding region for a peptide linker, wherein the coding region for a peptide linker is located between (a)(2) and (a)(3).

36. The library of claim 33 wherein the ribozyme RNA of (a)(1) is a contiguous sequence.

37. The library of claim 33 wherein the ribozyme RNA of (a)(1) comprises modified BIV-1 TAR RNA and the peptide tag is the Tat tag peptide or the Tat 2 tag peptide.

38. The library of claim 33 wherein each engineered mRNA additionally comprises a coding region for a peptide linker, wherein the coding region for the peptide linker is located between (a)(2) and (a)(3).

39. A method of producing a diverse library of encoded polypeptides, which comprises polypeptide-engineered mRNA conjugates, comprising the steps of:
  (a) combining:
    (1) a library of engineered mRNAs, wherein each engineered mRNA in the library comprises:
      (i) ribozyme RNA which specifically covalently links to a peptide tag in the presence of the remainder of the ribozyme sequence;
      (ii) a coding region for the peptide with which the ribozyme RNA of (a)(1)(i) specifically covalently links, wherein the peptide is referred to as a peptide tag;
      (iii) a coding region for a diverse polypeptide; and
      (iv) two PCR primer-binding sites; and
    (2) an appropriate in vitro translation mixture, thereby producing a combination;
  (b) maintaining the combination under conditions appropriate for translation of the engineered mRNA to occur, whereby the translation product of the engineered mRNA, which comprises the peptide tag and the diverse polypeptide segment, is produced and joined to the engineered mRNA by a covalent bond between the ribozyme RNA of the engineered mRNA and a reactive group of the peptide tag, thereby producing polypeptide-engineered mRNA conjugates.

40. The method of claim 39 wherein a region coding for a linker sequence is located between (a)(1)(ii) and (a)(1)(iii).

41. The method of claim 39 wherein the ribozyme RNA of (a)(1)(i) comprises at least 18 nucleotides.

42. The method of claim 39 wherein the ribozyme RNA of (a)(1)(i) is a contiguous sequence.

43. The method of claim 39 wherein the ribozyme sequence comprises SEQ ID NO.: 5 or SEQ ID NO.: 6.

44. The method of claim 39 wherein the ribozyme RNA of (a)(1)(i) comprises modified BIV-1 TAR RNA and the peptide tag is the Tat tag peptide or the Tat 2 tag peptide.

45. The method of claim 39 wherein each engineered mRNA additionally comprises a coding region for a peptide linker, wherein the region coding for the peptide linker is located between (a)(1)(ii) and (a)(1)(iii).

46. A method of identifying members of a diverse encoded polypeptide library which exhibit a desired activity, wherein members are polypeptide-engineered mRNA conjugates, comprising the steps of:
  (a) producing a diverse encoded polypeptide library which comprises polypeptide-engineered mRNA conjugates by:
    (i) combining:
      (1) a library of engineered mRNAs, wherein each engineered mRNA in the library comprises:
        (a) ribozyme RNA which specifically covalently links to a peptide;
        (b) a coding region for the peptide with which the RNA of (1)(a) interacts, wherein the peptide is referred to as a peptide tag;
        (c) a coding region for a diverse polypeptide; and
        (d) two PCR primer-binding sites; and
      (2) an appropriate in vitro translation mixture, thereby producing a combination;
    (ii) maintaining the combination under conditions appropriate for translation of the engineered mRNA to occur,
  whereby the translation product of the engineered mRNA, which comprises the peptide tag and the diverse polypeptide, is produced and joined to the engineered mRNA by a covalent bond between the 5' end of the engineered mRNA and a reactive group of the peptide tag, thereby producing polypeptide-engineered mRNA conjugates;
  (b) enriching the diverse encoded polypeptide library for members which exhibit a desired activity, thereby producing an enriched polypeptide library comprised of polypeptide-engineered mRNA conjugates;
  (c) amplifying the enriched encoded polypeptide library by:
    (i) reverse transcribing the engineered mRNA component of the conjugates, thereby producing the corresponding cDNA;
    (ii) amplifying and transcribing in vitro the corresponding cDNA, thereby producing a pool of amplified, enriched engineered mRNA;

(iii) combining the pool of amplified, enriched engineered mRNA with an appropriate in vitro translation mixture, thereby producing a combination; and (iv) maintaining the combination under conditions appropriate for translation of the engineered mRNA to occur, whereby the translation product of the engineered mRNA is produced and joined to the engineered mRNA by a covalent bond between the ribozyme RNA of the engineered mRNA and a reactive group of the peptide tag, thereby producing an amplified enriched polypeptide library comprised of polypeptide-engineered mRNA conjugates;

(d) repeating steps (b)–(c) as necessary until members which exhibit the desired activity are present in sufficient number to be detected; and (e) detecting members which exhibit the desired activity, thereby identifying members which exhibit the desired activity.

47. The method of claim 46 wherein the ribozyme RNA of (a)(i)(1)(a) is one nucleotide.

48. The method of claim 46 wherein the ribozyme RNA of (a)(i)(1)(a) is from 1 to about 18 nucleotide residues, inclusive, wherein the 1 to 18 nucleotide residues are from the 5' end of the ribozyme sequence.

49. The method of claim 46 wherein the ribozyme RNA of (a)(i)(1)(a) comprises at least 18 nucleotides.

50. The method of claim 46 wherein the ribozyme RNA of (a)(i)(1)(a) is a contiguous sequence.

51. The method of claim 46 wherein the ribozyme RNA of (a)(i)(1 )(a) comprises modified BIV-1 TAR RNA and the peptide tag is the Tat tag peptide or the Tat 2 tag peptide.

52. The method of claim 46 wherein the ribozyme RNA is the ribozyme of SEQ ID NO.: 5 or SEQ ID NO.: 6.

53. The method of claim 46 wherein the engineered mRNA further comprises a coding region for a linker, wherein the coding for the linker is located between (a)(i)(1)(b) and (a)(i)(1)(c).

54. A member of a diverse encoded polypeptide library which exhibits a desired activity, identified by the method of claim 46.

55. A polypeptide fragment of a polypeptide-engineered mRNA conjugate, wherein the polypeptide fragment comprises a diverse polypeptide and a peptide tag.

56. An engineered mRNA fragment of a polypeptide-engineered mRNA conjugate which comprises a) a ribozyme RNA which specifically covalently links to a peptide in the presence of the remainder of the ribozyme;

b) a coding region for the peptide with which the ribozyme RNA covalently links, wherein the peptide is referred to as a peptide tag;

c) a coding region for a diverse polypeptide; and d) two PCR primer-binding sites.

57. An isolated ribozyme that joins an mRNA to the translation product of the mRNA.

58. The isolated ribozyme of claim 57 that comprises:

a) SEQ ID NO.: 5;

b) SEQ ID NO.: 6; or c) SEQ ID NO.: 7 and SEQ ID NO.: 8.

59. The isolated ribozyme of claim 57 wherein the ribozyme comprises a nucleotide sequence sufficiently similar to SEQ ID NO.: 5 to result in the conformation of the ribozyme of SEQ ID NO. 5 or a nucleotide sequence sufficiently similar to SEQ ID NO.: 6 to result in the conformation of the ribozyme of SEQ ID NO.: 6.

60. A polypeptide-nucleic acid tag conjugate comprising:

(a) a polypeptide of interest;

(b) a peptide tag linked to the polypeptide of interest, wherein the peptide tag is the substrate of a ribozyme;

(c) a ribozyme or a segment of a ribozyme for which the peptide tag of (b) is a substrate, wherein the ribozyme or ribozyme segment is covalently linked to the peptide tag; and (d) a nucleic acid tag, wherein the nucleic acid tag is linked to the ribozyme or ribozyme segment.

61. A method of producing a polypeptide-nucleic acid tag conjugate of claim 60, comprising:

(a) combining:

(1) a polypeptide of interest which bears a peptide tag wherein the peptide tag is a substrate for ribozyme RNA;

(2) ribozyme RNA, wherein the ribozyme RNA specifically covalently links to the peptide tag of (a)(1) in the presence of the remainder of the ribozyme and has linked thereto a nucleic acid tag;

(3) the remainder of the ribozyme, thereby producing a combination; and (b) maintaining the combination under conditions appropriate for ribozyme RNA of (a)(2) to associate with ribozyme RNA of (a)(3), forming a functional ribozyme that specifically covalently links the peptide tag to ribozyme RNA of (a)(2), whereby a polypeptide-nucleic acid tag conjugate of claim 60 is produced.

62. A method of separating a polypeptide from a mixture of polypeptides, comprising:

(a) tagging the polypeptide at its amino terminus with a peptide tag, thereby producing a polypeptide-peptide tag, wherein the peptide tag is a substrate for ribozyme RNA, thereby producing a mixture comprising the polypeptide-peptide tag;

(b) combining the mixture produced in (a) with (1) ribozyme RNA which bears a nucleic acid tag and specifically covalently links to the peptide tag in the presence of the remainder of the ribozyme and (2) the remainder of the ribozyme, under conditions appropriate for ribozyme (b) (1) to specifically interact with its peptide substrate thereby forming a covalent link with the peptide and tagging the polypeptide with the nucleic acid tag, whereby a mixture comprising a polypeptide-nucleic acid tag conjugate is formed;

(c) combining the mixture formed in (b) with a nucleic acid which is a binding partner for the nucleic acid tag of the polypeptide-nucleic acid tag conjugate, whereby the binding partner hybridizes with the nucleic acid tag of the conjugate, forming a polypeptide-nucleic acid tag conjugate with the binding partner bound thereto; and (d) separating the polypeptide-nucleic acid tag conjugate with the binding partner bound thereto from the product of (c), whereby the polypeptide is separated from the mixture of polypeptides.

63. The method of claim 62 wherein the binding partner is bound to a solid surface.

64. A method of detecting a polypeptide of interest in a mixture wherein the polypeptide of interest is present in a polypeptide-nucleic acid tag conjugate, comprising:

(a) combining a mixture to be assessed for the presence of the polypeptide-nucleic acid tag conjugate with a binding partner for the nucleic acid tag, wherein the binding partner is a nucleic acid sequence sufficiently complementary to the nucleic acid tag that the binding partner and the nucleic acid tag of the conjugate bind to one another and remain bound under the condition used and;

(b) detecting whether binding of the nucleic acid tag and the binding partner occurred, wherein if binding is detected, the polypeptide of interest is detected.

65. The method of claim 64, wherein the binding partner or the nucleic acid tag is labeled with a detectable moiety.

* * * * *

SEQUENCE LISTING

<160> NUMBER OF SEQ ID NOS: 8

<210> SEQ ID NO 1
<211> LENGTH: 23
<212> TYPE: PRT
<213> ORGANISM: BIV-1

<400> SEQUENCE: 1

Met Ser Tyr Ser Gly Pro Arg Pro Arg Gly Thr Arg Gly Lys Gly Arg
 1               5                  10                  15

Arg Ile Arg Arg Gly Gly Lys
            20

<210> SEQ ID NO 2
<211> LENGTH: 23
<212> TYPE: PRT
<213> ORGANISM: BIV-1

<400> SEQUENCE: 2

Met Lys Tyr Ser Gly Pro Arg Pro Arg Gly Thr Arg Gly Lys Gly Arg
 1               5                  10                  15

-continued

```
Arg Ile Arg Arg Gly Gly Lys
            20

<210> SEQ ID NO 3
<211> LENGTH: 17
<212> TYPE: PRT
<213> ORGANISM: BIV-1

<400> SEQUENCE: 3

Ser Gly Pro Arg Pro Arg Gly Thr Arg Gly Lys Gly Arg Arg Ile Arg
 1               5                  10                  15

Arg

<210> SEQ ID NO 4
<211> LENGTH: 28
<212> TYPE: DNA
<213> ORGANISM: BIV-1

<400> SEQUENCE: 4
ggacagcucc gagcauucuc guguagcu                                         28

<210> SEQ ID NO 5
<211> LENGTH: 98
<212> TYPE: DNA
<213> ORGANISM: Artificial Sequence
<220> FEATURE:
<223> OTHER INFORMATION: ribozyme sequence

<400> SEQUENCE: 5
ggacagcucc gagcauucuc guguagcucu gaccauggag uacagcacca cgucgucgcu      60
gguauauggc caaguaauaa acgacucauc ccuccaag                              98

<210> SEQ ID NO 6
<211> LENGTH: 152
<212> TYPE: DNA
<213> ORGANISM: Artificial Sequence
<220> FEATURE:
<223> OTHER INFORMATION: Ribozyme sequence

<400> SEQUENCE: 6
ggacagcucc gagcauucuc guguagcucu gaccauggggg uaggcuugaa uucaguguuc     60
gacgauucac uaguuucgaa acauaaguca gccguauaua gucacuuugu caggcgccac    120
cuaggucgga ccugacaaug cauccccccca gg                                  152

<210> SEQ ID NO 7
<211> LENGTH: 18
<212> TYPE: DNA
<213> ORGANISM: Artificial Sequence
<220> FEATURE:
<223> OTHER INFORMATION: Ribozyme sequence

<400> SEQUENCE: 7
ggacagcucc gagugucc                                                    18

<210> SEQ ID NO 8
<211> LENGTH: 79
<212> TYPE: DNA
<213> ORGANISM: Artificial Sequence
```

-continued

```
<220> FEATURE:
<223> OTHER INFORMATION: Ribozyme sequence

<400> SEQUENCE: 8
ggacacucgu guagcucuga ccauggagua cagcuucggc ugguauaugg ccaaguacuu         60
cgguacucau cccuccaag                                                     79
```